United States Patent [19]

Ishizaka et al.

[11] Patent Number: 5,807,714

[45] Date of Patent: Sep. 15, 1998

[54] METHOD OF PRODUCTION OF ANTIGEN-SPECIFIC GLYCOSYLATION INHIBITING FACTOR

[75] Inventors: Kimishige Ishizaka; Yasuyuki Ishii, both of La Jolla, Calif.

[73] Assignee: La Jolla Institute for Allergy and Immunology, San Diego, Calif.

[21] Appl. No.: 416,336

[22] Filed: Apr. 4, 1995

[51] Int. Cl.[6] .............................. C12P 21/02; C12P 21/04
[52] U.S. Cl. ...................... 435/69.5; 435/69.7; 435/70.3
[58] Field of Search ................................. 435/69.1, 69.3, 435/69.5, 69.7, 69.8, 70.1, 70.2, 70.3

[56] References Cited

PUBLICATIONS

Mikayama et al., Proc. Natl. Acad. Sci. 90: 10056–10060, Nov. 1993.

Kuchroo et al., Proc Natl. Acad. Sci. 88: 8700–8704, Oct. 1991.

Fairchild et al., J. of Immunology, 145: 2001–2009, Oct. 1990.

Collins et al., Faseb Journal, 6: A1140, May 1992.

Thomas et al., J. of Immunology, vol. 148: 729–737, Feb. 1992.

*Primary Examiner*—Frank C. Eisenschenk
*Assistant Examiner*—Patrick Nolan
*Attorney, Agent, or Firm*—Fish & Richardson, P.C.

[57] ABSTRACT

A method for the recombinant production and for the isolation of antigen-specific glycosylation inhibiting factor (AgGIF) is provided. Also disclosed is a method for modulating the immune responses in an antigen-specific manner utilizing a AgGIF, comprising soluble non-specific GIF-TCRα chains which bind to the antigen, and which suppress the immune response in an antigen-specific fashion.

20 Claims, 8 Drawing Sheets

```
  1 ATGCAGAGGAACCTGGGAGCTGTGCTGGGGATTCTGTGGGTGCAGATTTGCTGGGTGAGC
  1  M  Q  R  N  L  G  A  V  L  G  I  L  W  V  Q  I  C  W  V  S
                            L

61 GGAGATAAGGTGAAGCAAAGTCCCTCAGCGCTGAGTCTCCAAGAAGGAACCAATTCTGCT
 21  G  D  K  V  K  Q  S  P  S  A  L  S  L  Q  E  G  T  N  S  A
              V

121 CTGAGATGCAATTTTTCTATCGCCGCGACAACTGTGCAGTGGTTCCTACAGAATCCCAGG
 41  L  R  C  N  F  S  I  A  A  T  T  V  Q  W  F  L  Q  N  P  R

181 GGCAGCCTCATGAATCTTTTTTACCTGGTTCCAGGAACAAAGGAGAATGGGAGGTTAAAG
 61  G  S  L  M  N  L  F  Y  L  V  P  G  T  K  E  N  G  R  L  K

241 TCAACATTCAATTCTAAGGAGAGCTACAGCACCCTGCACATCAGGGATGCCCAGCTGGAA
 81  S  T  F  N  S  K  E  S  Y  S  T  L  H  I  R  D  A  Q  L  E

301 GACTCAGGCACTTACTTCTGTGCTGCTGAGGGGGGAGGCAGCAATTACAAACTGACATTT
101  D  S  G  T  Y  F  C  A  A  E  G  G  G  S  N  Y  K  L  T  F
              V                          J

361 GGGAAAGGAACTCTCTTAACTGTGACTCCAAACATCCAGAACCCAGAACCTGCTGTGTAC
121  G  K  G  T  L  L  T  V  T  P  N  I  Q  N  P  E  P  A  V  Y
              J                          C

421 CAGTTAAAAGATCCTCGGTCTCAGGACAGCACCCTCTGCCTGTTCACCGACTTTGACTCC
141  Q  L  K  D  P  R  S  Q  D  S  T  L  C  L  F  T  D  F  D  S

481 CAAATCAATGTGCCGAAAACCATGGAATCTGGAACGTTCATCACTGACAAAACTGTGCTG
161  Q  I  N  V  P  K  T  M  E  S  G  T  F  I  T  D  K  T  V  L

541 GACATGAAAGCTATGGATTCCAAGAGCAATGGGGCCATTGCCTGGAGCAACCAGACAAGC
181  D  M  K  A  M  D  S  K  S  N  G  A  I  A  W  S  N  Q  T  S

601 TTCACCTGCCAAGATATCTTCAAAGAGACCAACGCCACCTACCCCAGTTCAGACGTTCCC
201  F  T  C  Q  D  I  F  K  E  T  N  A  T  Y  P  S  S  D  V  P

661 TGTGATGCCACGTTGACCGAGAAAAGCTTTGAAACAGATATGAACCTAAACTTTCAAAAC
221  C  D  A  T  L  T  E  K  S  F  E  T  D  M  N  L  N  F  Q  N

721 CTGTCAGTTATGGGACTCCGAATCCTCCTGCTGAAAGTAGCGGGATTTAACCTGCTCATG
241  L  S  V  M  G  L  R  I  L  L  L  K  V  A  G  F  N  L  L  M

781 ACGCTGAGGCTGTGGTCCAGTTGA
261  T  L  R  L  W  S  S  *
                 C
```

FIG. 2A

Murine GIF full length Sequence

```
                •           •           •           •          50           •
GGCACGACGTCAGGTCCCTGGCTTGGGTCACACCGCGCTTTGTACCGTCCTCCGGTCCAC

•           •           •          100           •           •
GCTCGCAGTCTCTCCGCCACCATGCCTATGTTCATCGTGAACACCAATGTTCCCCGCGCC
                     M  P  M  F  I  V  N  T  N  V  P  R  A
                     |---------------------------------------
                                                              |--
        •           •          150           •           •           •
TCCGTGCCAGAGGGGTTTCTGTCGGAGCTCACCCAGCAGCTGGCGCAGGCCACCGGCAAG
 S  V  P  E  G  F  L  S  E  L  T  Q  Q  L  A  Q  A  T  G  K
-----|
_____|
        •          200           •           •           •           •
CCCGCACAGTACATCGCAGTGCACGTGGTCCCGGACCAGCTCATGACTTTTAGCGGCACG
 P  A  Q  Y  I  A  V  H  V  V  P  D  Q  L  M  T  F  S  G  T

250           •           •           •           •          300
AACGATCCCTGCGCCCTCTGCAGCCTGCACAGCATCGGCAAGATCGGTGGTGCCCAGAAC
 N  D  P  C  A  L  C  S  L  H  S  I  G  K  I  G  G  A  Q  N
    |---------------------------------------|
                                             |-----------------
        •           •           •          350           •
CGCAACTACAGTAAGCTGCTGTGTGGCCTGCTGTCCGATCGCCTGCACATCAGCCCGGAC
 R  N  Y  S  K  L  L  C  G  L  L  S  D  R  L  H  I  S  P  D
_____|                            |-----------------
        •           •           •          400           •           •
CGGGTCTACATCAACTATTACGACATGAACGCTGCCAACGTGGGCTGGAACGGTTCCACC
 R  V  Y  I  N  Y  Y  D  M  N  A  A  N  V  G  W  N  G  S  T
--------------------||---------------------
        •           •          450           •           •           •
TTCGCTTGAGTCCTGGCCCCACTTACCTGCACCGCTGTTCTTTGAGCCTCGCCTCTCCAC
 F  A  *
------|
        •          500           •           •           •           •
GTAGTGTTCTGTGTTTATCCACCGGTAGCGATGCCCACCTTCCAGCCGGGAGAAATAAAT
       550           •           •           •           •          600
GGTTTATAAGAGACCAAAAAAAAAAAAAAAAAAAAAAAAAAAAAAAAAAAAAAAAAAAAA
        •           •           •
AAAAAAAAAAAAAAAAAAAAAAAAAAAAAAAAA
```

FIG. 2C

Human GIF cDNA full length Sequence

```
                  •                   •                   •                   •           50                •
CAGGCACGTAGCTCAGCGGCGGCGCGGCGCGTGCGTCTGTGCCTCTGCGCGGGTCTCCTG

•                   •                   •                  100                •                •
GTCCTTCTGCCATCATGCCGATGTTCATCGTAAACACCAACGTGCCCCGCGCCTCCGTGC
                 M   P   M   F   I   V   N   T   N   V   P   R   A   S   V

•                   •         SacI150                   •                   •                •
CGGACGGGTTCCTCTCCGAGCTCACCCAGCAGCTGGCGCAGGCCACCGGCAAGCCCCCCC
 P   D   G   F   L   S   E   L   T   Q   Q   L   A   Q   A   T   G   K   P   P

•          200                   •                   •                   •                •
AGTACATCGCGGTGCACGTGGTCCCGGACCAGCTCATGGCCTTCGGCGGCTCCAGCGAGC
 Q   Y   I   A   V   H   V   V   P   D   Q   L   M   A   F   G   G   S   S   E

250        Pst1   •                   •                   •                   •               300
CGTGCGCGCTCTGCAGCCTGCACAGCATCGGCAAGATCGGCGGCGCGCAGAACCGCTCCT
 P   C   A   L   C   S   L   H   S   I   G   K   I   G   G   A   Q   N   R   S

•                   •                   •                   •          350                •
ACAGCAAGCTGCTGTGCGGCCTGCTGGCCGAGCGCCTGCGCATCAGCCCGGACAGGGTCT
 Y   S   K   L   L   C   G   L   L   A   E   R   L   R   I   S   P   D   R   V

•                   •                   •          400                   •                •
ACATCAACTATTACGACATGAACGCGGCCAATGTGGGCTGGAACAACTCCACCTTCGCCT
 Y   I   N   Y   Y   D   M   N   A   A   N   V   G   W   N   N   S   T   F   A

•                   •          450                   •SmaI                •                •
AAGAGCCGCAGGGACCCACGCTGTCTGCGCTGGCTCCACCCGGGAACCCGCCGCACGCTG
 *
                  •          500                   •                   •                   •                •
TGTTCTAGGCCCGCCCACCCCAACCTTCTGGTGGGGAGAAATAAACGGTTTAGAGACTAA
         550
AAAAAAAAAAAAAAAAA
```

FIG. 2D

METHOD OF PRODUCTION OF ANTIGEN-SPECIFIC GLYCOSYLATION INHIBITING FACTOR

This invention was made with Government support under Grant No. AI11202 awarded by the National Institutes of Health. The Government has certain rights in this invention.

BACKGROUND OF THE INVENTION

1. Field of the Invention

This invention relates generally to the immune response and specifically to antigen-specific glycosylation inhibiting factor (AgGIF) which is useful for suppression of the immune response to a specific antigen.

2. Description of Related Art

Immunologists and others have long studied the immune system in an attempt to find a mechanism for regulating the immune response. To this end, various drugs or protocols have been utilized which either depress or augment the immune response in a non-specific fashion. However, this type of regulation is not satisfactory because it affects the entire immune system and it is not based on an understanding of the particular components of the immune system that would permit antigen specific regulation of an immune response. For example, in the treatment of allergies it would be advantageous to selectively suppress an immune response to a particular allergen without depressing the individual's entire immune system.

The introduction of a foreign antigen into an individual elicits an immune response consisting of two major components, the cellular and humoral immune responses, mediated by functionally distinct populations of lymphocytes known as T and B cells, respectively. T cells respond to antigen stimulation by producing lymphokines which "help" or activate various other cell types in the immune system. In addition, certain T cells can become cytotoxic effector cells. On the other hand, the B cell response primarily consists of their secretory products, antibodies, which directly bind to antigens.

A salient feature of both B and T cell responses is their exquisite specificity for the immunizing antigen, however, the mechanisms for antigen recognition differ. Antibodies bind directly to antigens on a solid surface or in solution, whereas T cells only react with antigens that are present on a solid phase such as the surfaces of antigen-presenting cells. Additionally, the antigens must be presented to T cells in the context of major histocompatibility complex (MHC)-encoded class I or class II molecules. The MHC refers to a cluster of genes that encode proteins with diverse immunological functions. Class I gene products are found on all cells and they are the targets of major transplantation rejection responses. Class II gene products are mostly expressed on cells in various hematopoietic lineages and they are involved in cell-cell interactions in the immune response. Both Class I and Class II proteins have been shown to also function as receptors for antigens on the surface of antigen-presenting cells.

In 1970, Gershon and Kondo (*Immunology* 18:723, 1970) proposed that T cells could also negatively influence the course of an immune response. Although this concept of immune regulation was initially met with skepticism, antigen-specific suppressor T cells (Ts) have been reported in a wide variety of experimental systems (Green, et al., *Ann. Rev. Immunol.* 1:439–463, 1983; Dorf and Benacerraf, *Ann. Rev. Immunol.* 2:127–158, 1984).

Attempts to delineate the mechanism of Ts action led to the discovery of a number of soluble mediators in T cell culture supernatants. It was therefore postulated that Ts functioned through the release of T suppressor factors (TsF) which then acted on other T and B cells. Elaborate models had been proposed based on experimental data to illustrate the complex interactions between different Ts subsets and their TsF (Asherson, et al., *Ann. Rev. Immunol.* 4:37–68, 1986).

Since specific cell surface markers had been identified for distinct functional subsets of T cells, a search for unique markers for Ts and their TsF was undertaken. A study of Ts surface phenotype first showed that they expressed CD8 (Lyt-2), a marker shared by T cells with cytotoxic potential. In 1976, an antiserum was reported that appeared to react with a structure specifically expressed by Ts in mice (Murphy, et al., *J Exp. Med.* 144:699, 1976; Tada, et al., *J Exp. Med,* 144:713, 1976). Mapping studies of the gene encoding the antigen localized it to the I region between I-Eα and I-Eβ within the murine MHC. This locus was called I–J.

In the early 1980's, the field of cellular immunology began to move from phenomenology to molecular characterization. This transition resulted in a number of discoveries such as the characterization of the T cell receptor (TCR), the identification of various lymphokines, and the elucidation of the three dimensional structure of MHC proteins. However, application of molecular cloning techniques to the study of T cell-mediated suppression did not yield fruitful insights. For instance, attempts to biochemically purify TsF to homogeneity had been largely unsuccessful. When the genes of the I region of the mouse MHC were isolated and sequenced, there did not appear to be enough DNA between I-Eα and I-Eβ to account for the I–J gene. Moreover, when a large panel of T cell clones and T cell hybridomas were examined for TCR β gene rearrangements, only helper and cytotoxic T cells contained such rearrangements while all Ts tested were negative, indicating that Ts might not express functional receptors (Hedrick, et al., *Proc. Natl. Acad. Sci. USA* 82:531–535, 1985).

The specificity of T and B cell responses for antigen is a function of the unique receptors expressed by these cells. Progress in the study of the B cell receptor advanced rapidly when it was found that B cells secreted their receptors in the form of antibodies.

Plasmacytomas are naturally-occurring tumors of antibody-producing cells that are monoclonal in origin. These tumors provided a continuous source of homogeneous proteins which were used in the initial purification and characterization of the structure of the antibody molecule (Potter, *Physiol. Res.* 52:631–710, 1972). It has now been proven that antibodies are identical to their membrane-bound counterparts except that the cell surface form contains a domain for transmembrane anchoring (Tonegawa, *Nature* 302:575–581, 1983).

Early work on the TCR, on the other hand, failed to detect a secretory form of the TCR and, therefore, the approaches used with soluble antibodies could not be effectively employed. In addition, the discovery of MHC-restriction in T cell recognition of antigen added another level of difficulty to the analysis of the TCR (Zinkernagel and Doherty, *Nature* 248:701–702, 1974). At that time it was debatable whether a single TCR could account for binding to both antigen plus MHC or two separate receptors were involved. However, what seemed clear was that the TCR was unlikely to be identical to the B cell receptor.

The advent of the development of monoclonal antibodies; recombinant DNA technology and methods for long-term culture of antigen-specific T cells greatly facilitated the identification of the TCR in the 1980's. Monoclonal antibodies generated against clonal populations of T cells were found to specifically react with only the immunizing T cells (Allison, et al., *J. Immunol.* 129:2293, 1982; Haskin, et al., J. Exp. Med. 157:1149, 1983; Samelson, et al., *Proc. Natl. Acad. Sci.* USA 80:6972, 1983). The use of these clonally-specific antibodies to immunoprecipitate T cell membranes revealed a 46,000 dalton molecular weight band by SDS-PAGE. Under non-reducing conditions, a 90,000 dalton band was detected suggesting a dimeric structure for the TCR. Subsequent experiments established that a functional TCR is a heterodimer composed of two disulphide-linked glycoproteins known as $\alpha$ and $\beta$ (Marrack and Kappler, *Science* 238:1073–1079, 1987). At about the same time, complementary DNA (cDNA) clones encoding the $\alpha$ and $\beta$ chains were isolated in both human and mice (Hedrick, et al., *Nature* 308:149–153, 1984; Hedrick, et al., *Nature* 308:153–158, 1984; Yanagi, et al., *Nature* 308:145–149, 1984). Sequence analysis of the cDNA demonstrated that the coding sequences were made up of rearranged gene segments similar to that of antibodies. Transfer of the $\alpha$ and $\beta$ genes into recipient cells was shown to be both necessary and sufficient to confer antigen specificity and MHC-restriction (Dembic, et al., *Nature* 320:232–238, 1986). Thus, the heterodimeric TCR appears to be responsible for recognizing the combination of antigen and MHC. While some studies suggest that the $\alpha$ and $\beta$ variable regions are skewed towards recognition of antigen and MHC, respectively (Kappler, et al., *Cell* 49:263–271, 1987; Winoto, et al., *Nature* 324:679–682, 1986; Tan, et al., *Cell* 54:247–261, 1988), other studies suggest that recognition is an emergent property of the entire receptor (Kuo and Hood, *Proc. Natl. Acad. Sci.* USA 84:7614–7618, 1987; Danska, et al., *J Exp. Med.* 172:27–33, 1990).

CD3 is a complex of polypeptides which are non-covalently linked to the TCR and which may be involved in transmembrane signalling events leading to T cell activation triggered by TCR occupancy (Clevers, et al, *Ann. Rev. Immunol.* 6:629., 1988). Direct stimulation of CD3 with antibodies has been shown to mimic the normal pathways of T cell activation (Meuer, et al., *J. Exp. Med.* 158:988, 1983). The transport of CD3 to the T cell surface requires its association with complete heterodimeric TCR complexes intracellularly. It has also been demonstrated that complexes of both TCR $\alpha$ and $\beta$ chains and the CD3 polypeptides are assembled in the endoplasmic reticulum (Minami, et al., *Proc. Natl. Acad. Sci.* USA 84:2688–2692, 1987; Alarcon, et al, *J. Biol. Chem.* 236:2953–2961, 1988). The correctly formed complete receptors, TCR/CD3, are then transported to the cell surface as a functional unit. The incompletely assembled receptor complexes are degraded in the endoplasmic reticulum or transported through the Golgi to lysosomes where they become degraded. Therefore, unlinked $\alpha$ and $\beta$ chains do not appear to normally gain access to the exterior of T cells. Even complete TCR $\alpha$ and $\beta$ receptors are not readily detectable in secreted forms extracellularly. Heretofore, their function in antigen recognition was thought to be limited to the T cell surface and in the form of a heterodimer.

It is now clear that the $\alpha\beta$ TCR is expressed by the vast majority of functional T cells. Although a second type of TCR composed of $\gamma\delta$ heterodimer has been identified, these receptors are expressed by a small percentage of peripheral T cells and their involvement in antigen-specific recognition is yet to be demonstrated. Structurally, the $\alpha\beta$ and $\gamma\delta$ receptors of T cells are highly homologous to antibody molecules in primary sequence, gene organization and modes of DNA rearrangement (Davis and Bjorkman, *Nature* 334:395–402, 1988). However, the T cell antigen receptors are distinct from antibodies in two major aspects: TCR are only found at cell surfaces and they recognize antigens only in the context of MHC-encoded molecules.

Recent studies suggest that the TCR may, in some occasions, be shed or released from cells (Guy, et al., *Science* 244:1477–1480, 1989; Fairchild, et al., *J. Immunol.* 145:2001–2009, 1990). However, it has not been demonstrated whether such secreted molecules are complete TCR, partial fragments, or other molecules with TCR cross-reactive epitopes. Prior to the discoveries demonstrated by the examples described herein, the notion that functionally active TCR$\alpha$ chains could be released from T cells independently of the remaining TCR components was controversial and met with skepticism. Klausner and colleagues (Bonifacino, et al., *Science* 247:79–82, 1990) have shown that TCR$\alpha$ is retained and degraded in the endoplasmic reticulum unless complexed with CD3$\delta$, and further (Minami, et al., *Proc. Natl. Acad. Sci.* USA 84:2688–2692, 1987) that TCR$\alpha$ that is not exported to the cell surface as part of the CD3-TCR complex is degraded in lysosomes. These observations argue against a pathway whereby TCR$\alpha$ might be released from cells. Studies on TCR$\beta$, which is similarly retained and degraded in the endoplasmic reticulum (Wileman, et al., *Cell Regulation* 1:907–919, 1990), suggest that the assembly and transport of TCR is more complex. For example, in SCID mice expressing a TCR$\beta$ transgene, TCR$\beta$ is expressed on the surface of immature thymocytes in the absence of TCR$\alpha$ or CD3 components (Kishi, et al., *EMBO J.* 10:93–100, 1991). Further, a truncated TCR$\beta$ chain gene has been constructed, including only VDJ and the C$\beta_1$ domain, that is secreted despite the expectation that such a molecule should be degraded (Gascoigne, *J. Biol. Chem.* 265:9296–9301, 1990). Thus, the possibility existed that in some cells, TCR might be released in small quantities, possibly in a complex with other unidentified molecules and/or in a post-translationally truncated form.

A number of experimenters reported the presence of an unidentified soluble regulatory factor or factors which reacted with antibodies to TCR$\alpha$. For example, a cell free immunoregulatory activity was detected in an in vitro assay of a CD4$^+$ helper T cell hybridoma, A1.1, specific for a synthetic polypeptide antigen, poly 18, plus I-A$^d$; the antigen fine specificity of the factor corresponded to that of the T cell hybridoma (Zheng, et al., *J. Immunol.* 140:1351–1358 1988). Antisense oligonucleotides corresponding to TCR V$\alpha$ and V$\beta$ were found to specifically inhibit cell surface TCR-CD3 expression, but only antisense for V$\alpha$ and not V$\beta$ (or control oligonucleotides) inhibited the production of the soluble regulatory activity of A1.1 (Zheng, et al., *Proc. Natl. Acad. Sci.* USA 86:3758–3762, 1989). In a very recent study, the antigen-specific regulatory activity of A1.1 was bound and eluted from a monoclonal antibody column specific for TCR $\alpha$ and resolved as a 46,000 dalton molecular weight protein from metabolically-labeled supernatants; the activity was not bound by anti-TCR$\beta$, anti-TCR V$\beta$, or anti-CD3$\epsilon$ antibodies (Bissonnette, et al., *J. Immunol.* 146:2898–2907, 1991). Ts activities not derived from surface TCR, although sharing TCR$\alpha$-chain determinants, were reported but not characterized (Collins, et al., *J. Immunol.* 145:2809–2812, 1990). Takada, et al., *J. Immunol.* 145:2846–2853, 1990) also reported a Ts activity which shared TCR$\alpha$-chain determinants, but which was MHC restricted. In contrast to these results, Fairchild, *J. Immunol.* 145:2001–2009, 1990) reported a DNP-specific Ts factor which reacted with anti-TCR Cα but which also reacted with anti-Vβ and anti-TCR-β antibodies. Prior to the discoveries described herein, no one had identified or elucidated the role of TCRα as a soluble, immunoregulatory mediator responsible for the observed antigen-specific regulatory activity.

Three main strategies, which replace or delete the TCR transmembrane region, have been attempted for the production of soluble TCR molecules. In the most straightforward approach, translational termination codons were introduced upstream of the TCRα or TCRα/β dimers. In cDNA-transfected COS-1 cells, COS-7 cells or Hela cells, TCRα has been reported to be rapidly degraded in a nonlysosomal compartment before entering the Golgi apparatus (Wileman, et al., *J. Cell. Biol.*, 110:973–986, 1990; Lippincott-Schwartz, et al., *Cell*, 54:209–220, 1988; Baniyash, et al.,*J. Biol. Chem.*, 263:9874–9878, 1988; Bonifacino, et al., *Science*, 247:79–82, 1990; Bonifacino, et al., *Cell*, 63:503–513, 1990; Manolios, et al., *Science*, 249:274–277, 1990; Shin, et al., *Science*, 259:1901–1904, 1993). In the second strategy, the extracellular V and C domains of the TCRα and β chains have been shuffled to the glycosyl-phosphatidylinositol membrane anchor of the placental alkaline phosphatase or Thy-1 molecules (Lin, et al., *Science*, 249:677–679, 1990; Slanetz, et al., *Eur. J. Immunol.*, 21:179–183, 1991). The corresponding lipid-linked TCR polypeptides were released from the membrane in soluble form by treatment of the cells with phosphatidylinositol-specific phospholipase C, and the solubilized TCRαβ heterodimers were shown to react specifically with an anti-clonotypic monoclonal antibody. However, the yield of released TCR polypeptides was too low to apply this molecule for clinical use. The third approach was to engineer hybrid proteins of TCR with immunoglobin constant region (Gregoire, et al.,*Proc. Natl. Acad. Sci., USA*, 88:8077–8081, 1991; Weber, et al., *Nature*, 356:793–796, 1992) and CD3 zeta chain (Engel, et al., *Science*, 256:1318–1321, 1992). These fusion proteins were secreted into the medium by transfection of myeloma cells or leukemic cells, and these soluble TCRs were shown to retain all serologically detected epitopes of the corresponding cell-surface-bound TCR. However, these fusion proteins showed low-affinity recognition of antigens and may be immunogenic. However, despite all of the studies which have been done on the role of TCRα, prior to the present invention TCRα was previously known to exist in association with other TCR subunits, such as part of the membrane bound TCR.

An example of where the suppression from immune response would be described is in the treatment of allergies. It has been established that IgE antibodies against allergens cause hay fever, and are involved in the other allergic diseases such as extrinsic asthma. The crucial role of IgE antibodies in the allergic diseases raised the possibility that the regulation and suppression of the IgE antibody formation against allergens would be one of the fundamental treatments for allergic diseases. For example, in the serum of hay fever patients sensitive to ragweed allergens, IgE antibodies against the allergens are always detected. The IgE antibody titer goes up after the pollen season, and then declines only slightly during the rest of the year. Since the half life of IgE in the serum is only 2 to 3 days, the persistence of the IgE antibody titer indicates that the antibodies are being synthesized continuously by the lymphoid cells of the patients in spite of the lack of allergen exposure.

Over the past 20 years, several different attempts were made to control the IgE antibody response in experimental animals. One of the approaches was to improve classical immunotherpy or desensitization treatment, in which allergic patients receive repeated injections of a minute dose of allergen. It was shown that the desensitization treatment can improve clinical symptoms in some patients. However, the IgE antibody titer in the serum of hay fever patients did not decline after the treatment. The major immunological effects of the treatment is believed to be an enhancement of the IgG antibody formation, and the suppression of an increase in the IgE antibody titer after the pollen season.

A limitation in the desensitization, or immunosuppression treatment is that patients cannot tolerate a large dose of allergen because of side effects. In order to overcome this difficulty, attempts were made to use a chemically modified allergen, such as urea-denatured antigen or polyethylene glycol (PEG)-conjugates of the antigen for the treatment. Since the modified antigens do not bind to antibodies against the native antigen, relatively large doses of the modified antigen can be injected without causing allergic symptoms. However, the modified antigen can stimulate antigen-specific T-cells. Evidence was obtained that intravenous injections of the modified antigen into mice resulted in the generation of antigen-specific suppressor T-cells which suppressed the primary IgE antibody response to the native antigen. However, the treatment had minimal effects on the on-going IgE antibody formation, if the treatment were initiated after the antibody titer reached maximum (Takatsu and Ishizaka, *J. Immunol.*, 117:1211, 1976). In agreement with the observations in the mouse, clinical trials of polyethylene-glycol-conjugated allergen in hay fever patients showed that the treatment failed to diminish the IgE antibody titer. Failure of the repeated injections of the modified antigen to suppress the on-going IgE antibody formation is probably due to the presence of a relatively large population of antigen-specific helper T-cells in the allergic patients. Since the modified antigen not only induces the generation of antigen-specific suppressor T-cells, but also expands the population of helper T-cells, this latter effect of the treatment might have overcome the effect of suppressor T-cells. This interpretation is supported by the fact that transfer of antigen-specific suppressor T-cells into immunized mice resulted in the suppression of the on-going IgE antibody formation (Takatsu and Ishizaka, *J. Immunol.*, 117:1211, 1976). The results collectively suggested that the persistent IgE antibody formation in hay fever patients could be suppressed, if it were possible to generate the antigen-specific suppressor T-cells without expanding the helper T-cell populations.

Two types of T-cell factors have been found which have affinity for IgE and selectively regulate IgE synthesis. One of the IgE-binding factors (IgE-BF) selectively enhances the IgE response, while the other type of IgE-BF selectively suppresses the response. The major difference between the IgE-potentiating factors and IgE-suppressive factors appears to be carbohydrate moieties in the molecules. The IgE-potentiating factors bind to lentil lectin and concanavalin A, while IgE-suppressive factors fail to bind to these lectins (Yodoi, et al., *J. Immunol.*, 128:289, 1982). Analysis of the cellular mechanism for the selective formation of either IgE-potentiating factors or IgE-suppressive factors, as well as gene cloning of the factors, indicated that the IgE-potentiating factor and IgE-suppressive factor share a common structural gene and that the nature of the carbohydrate moieties and biologic activities of the factors are established during the post-translational glycosylation process (Martens, et al, *Proc. Nat'l Acad. Sci., U.S.A.*, 84:809, 1987). Under the physiological conditions, this glycosylation process is controlled by two T-cell factors which either enhance or inhibit this process. These factors are denominated glycosylation inhibiting factor (GIF) and glycosylation enhancing factor (GEF).

A unique property of GIF is its biochemical activity. This lymphokine binds to monoclonal antibodies against lipomodulin (a phospholipase inhibitory protein) (Uede, et al., *J. Immunol.*, 130:878, 1983). It was also found in the mouse that the major source of GIF is antigen-specific suppressor T-cells (Ts) (Jadieu, et al., *J. Immunol.*, 133:3266, 1984). Subsequent experiments on ovalbumin (OVA)-specific suppressor T-cell hybridomas indicated that stimulation of the hybridoma cells with antigen (OVA)-pulsed syngeneic macrophages resulted in the formation of GIF that has affinity for OVA (antigen-binding GIF). However, the same hybridomas constitutively secreted GIF having no affinity for OVA (nonspecific GIF). Studies on the relationship between non-specific GIF and OVA-binding GIF indicated that the antigen-binding GIF is composed of an antigen-binding polypeptide chain and a nonspecific GIF (Jardieu and Ishizaka, in *Immune Regulation By Characterized Polypeptides,* Goldstein, et al., eds., Alan R. Liss, Inc., N.Y., p595, 1987). It was also found that the antigen-binding GIF shares common antigenic determinants with antigen-specific suppressor T-cell factors (TsF) described by the other investigators, and suppressed the antibody response in an antigen (carrier)-specific manner. Furthermore, not only antigen-binding GIF, but also antigen-specific TsF described by other investigators, bound to immunosorbent coupled with monoclonal anti-lipomodulin (141-B9), and were recovered by elution of the immunosorbent at acid pH (Steele, et al., *J. Immunol.*, 142:2213, 1989).

Despite the major limitations of desensitization in treating allergy, this technique continues to be the method of choice. Consequently, there is significant need for a technique which is antigen-specific yet does not have associated with it the side effects seen with existing desensitization regimens.

The suppression of the immune response is crucial in order to prevent host versus graft (HVG) and graft versus host rejection (GVH). Unfortunately, in the case of both autoimmune disease as well as in HVG and GVH, the immune response suppression uses highly toxic drugs which are of limited effectiveness and act systemically, rather than specifically. The severe limitations of such therapy point to the need for immunosuppressive agents which have less toxicity, but greater specificity. The present invention provides a means for accomplishing this result.

SUMMARY OF THE INVENTION

The present invention is based on the discovery that TCRα not only plays a role in the formation of antigen-specific GIF (AgGIF) chains which directly bind to an antigen and suppress the immune response generated against that antigen, but that AgGIF is actually an expression product of the TCRα chain gene. Previously it was unknown that a particular TCRα imparted specificity to non-specific GIF after being expressed as a single polypeptide. Consequently, the present invention, for the first time, provides a method for isolating a polynucleotide which encodes antigen-specific GIF polypeptide and a method for isolating substantially pure antigen-specific GIF polypeptide.

DETAILED DESCRIPTION OF THE INVENTION

Figures 1A, 1B, 1C:
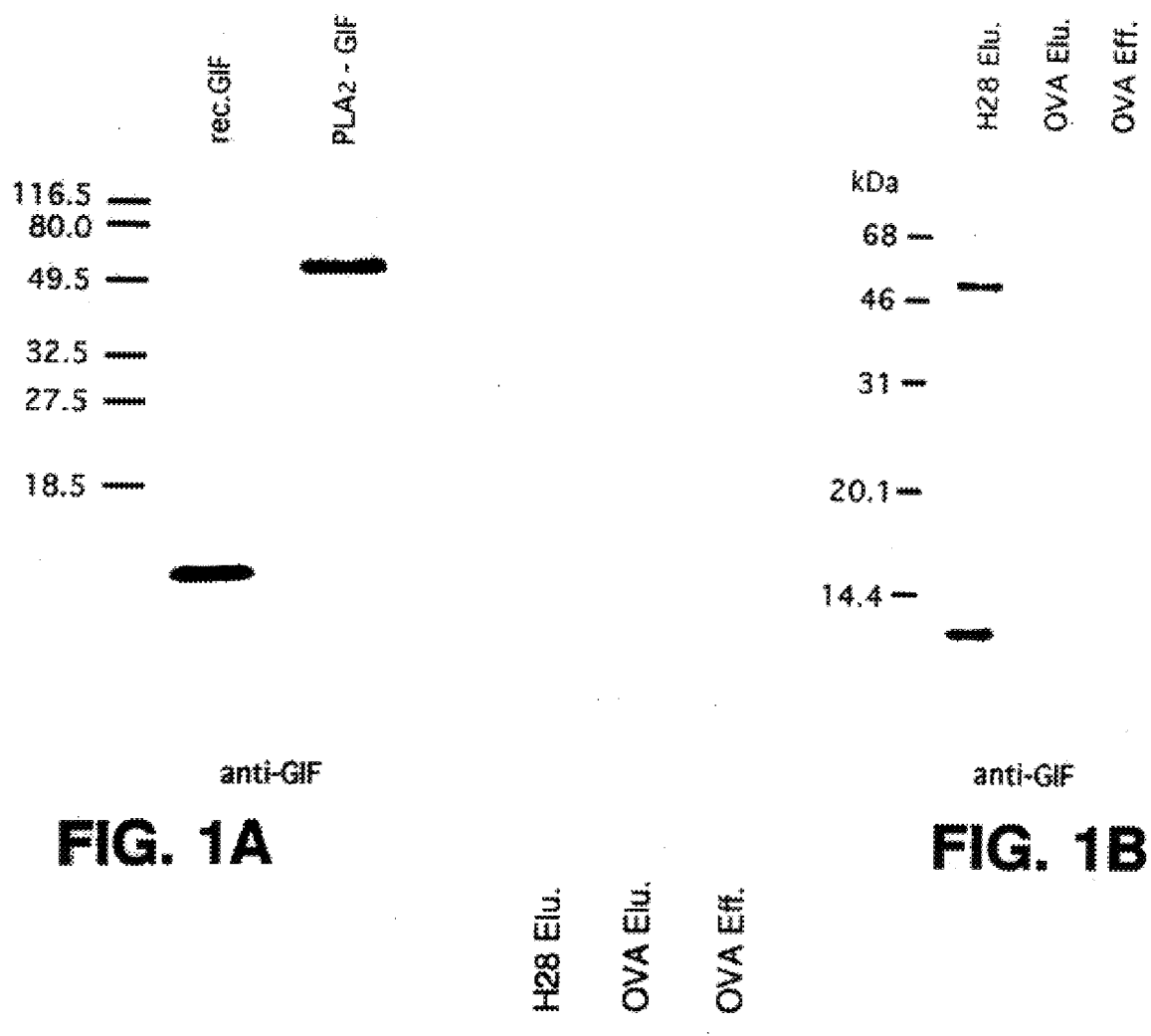
FIG. 1*a, b* and *c* show an immunoblot analysis of antigen-specific GIF from Ts hybridomas.

The present invention involves the production, isolation, and use of antigen-specific GIF for regulation of antigen-specific immune responses. For example, hypersensitivity reactions, autoimmune responses and graft rejection responses may be suppressed using antigen-specific GIF which is specific for the corresponding antigen, and which induces antigen-specific suppression.

The present invention relates to a polypeptide which includes non-specific GIF and a TCRα chain (not the complete T cell surface antigen receptor of α and β) possessing both antigen-binding and immunoregulatory activities. An antigen-binding GIF-TCRα protein with antigen-specific regulatory activity, called antigen-specific GIF (AgGIF), may be produced in a variety of ways. For example, expression of AgGIF protein may be achieved by recombinant DNA technology and/or chemical synthetic techniques based on known amino acid sequences. Alternatively, AgGIF may be purified directly from culture supernatants of continuous T cell lines that release this activity. While not wanting to be bound by a particular theory, it is likely that GIF and TCRα chains are transcribed and translated from a single polynucleotide or more than one polynucleotide which is transcribed and translated simultaneously. If the latter is true, the two polypeptides can be conjugated to form AgGIF.

In a first embodiment, the invention provides a method for isolating a polynucleotide(s) which encodes AgGIF polypeptide comprising activating a suppressor T cell, wherein activation induces AgGIF gene expression in the T cell, contacting suppressor T cell polynucleotides with an oligonucleotide which hybridizes to non-specific GIF polynucleotide and an oligonucleotide which hybridizes to TCRα polynucleotide, and isolating the polynucleotide which hybridizes to both non-specific GIF oligonucleotide and TCRα oligonucleotide.

The term "activating" refers to stimulation of the T cell to induce the production of AgGIF. Preferably, the suppressor T cell is activated by cross-linking the CD3 or T-cell surface receptors or exposing the cell to antigen-pulsed syngeneic macrophages, wherein the antigen is the antigen to which the AgGIF binds.

The method for isolating a polynucleotide which encodes AgGIF polypeptide includes contacting T suppressor cell DNA or RNA with an oligonucleotide probe which specifically hybridizes with non-specific GIF and an oligonucleotide probe which hybridizes with TCRα chain. Specifically, the polynucleotide encoding AgGIF hybridizes with the oligonucleotide probe from the constant region of the TCRα chain. The isolation of a polynucleotide encoding AgGIF, as described herein, wherein "contacting" relies on nucleic acid hybridization, makes it possible to isolate any AgGIF gene sequence from any organism, provided the appropriate probe is available. Oligonucleotide probes, which correspond to a part of the sequence encoding the GIF or TCRα chain constant region, can be synthesized chemically, for example. This requires that short, oligopeptide stretches of amino acid sequence must be known. For such screening, hybridization is preferably performed on mRNA, single-stranded DNA, or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucl. Acid Res., 9:879, 1981).

Preferably, the GIF probe is derived from the sequence as in SEQ ID NO: 1 or 3 (murine and human GIF polynucleotide, and FIG. 2c and d respectively), which correspond to the nucleotide sequence of human and murine GIF, respectively. One of skill in the art will be able to determine an appropriate oligonucleotide which could be utilized as a probe for hybridization to a putative AgGIF polynucleotide. Preferably, the oligonucleotide probe used for hybridization to the constant region of the TCRα chain is derived from SEQ ID NO: 5, which illustrates the TCRα chain constant region. Preferably the probe is about 15–25 nucleotides in length, however, longer or shorter probes can be designed, provided they allow specific hybridization under stringent conditions.

The polynucleotide encoding AgGIF which is isolated by the method of the invention may be either DNA or RNA. For example, the polynucleotide may be genomic DNA, cDNA or messenger RNA. Both messenger RNA (mRNA) for the preparation of cDNA as well as genomic sequences for AgGIF may be obtained from cell sources that produce the desired AgGIF. As part of the discovery in the present invention, it is now apparent that genomic sequences for AgGIF cannot be obtained from any non-activated cell source. While not wanting to bound by a particular theory, it appears that upon antigen stimulation, there is a rearrangement or translocation of the GIF or TCRα chain genes such that the two are now juxtaposed and are transcribed as a single molecule, whereby the TCRα chain gives the AgGIF polylpeptide the antigen specificity.

It is understood that all polynucleotides encoding all or a portion of the fusion polypeptide are also included herein, as long as they encode a polypeptide of which the cleavage product has biological activity of AgGIF. Such polynucleotides include naturally occurring, synthetic, and intentionally manipulated polynucleotides. For example, the AgGIF polynucleotide may be subjected to site-directed mutagenesis. The polynucleotide sequence also includes antisense sequences and sequences that are degenerate as a result of the genetic code. There are 20 natural amino acids, most of which are specified by more than one codon. Therefore, all degenerate nucleotide sequences are included in the invention as long as the amino acid sequence of the fusion polypeptide encoded by the nucleotide sequence is functionally unchanged. cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al., Nucl. Acid Res. 11:2325, 1983).

A cDNA expression library, such as lambda gt11, can be screened indirectly for expression of a polypeptide having at least one epitope, using antibodies specific for the polypeptide. Such antibodies can be either polyclonally or monoclonally derived and used to detect expression product indicative of the presence of protein encoded by the cDNA.

DNA sequences encoding the AgGIF polypeptide of the invention can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

T cells may be utilized as either the source of the coding sequences for the antigen specific GIF, and/or to prepare cDNA or genomic libraries. Additionally, parts of lymphoid organs (e.g., spleens, lymph nodes, thymus glands, and peripheral blood lymphocytes) may be ground and used as the source for extracting DNA or RNA.

The invention also provides polynucleotides which are complementary to the nucleotide sequences of the invention. A "complementary" nucleotide sequence will hybridize to a specific nucleotide sequence under conditions which allow the complementary sequence to hybridize. These conditions include temperature, pH, buffer and nucleotide composition. For example, the positive and negative strands of a double-stranded DNA molecule are complementary nucleotide sequences. Polynucleotides of the invention include fragments which are at least 15 bases in length, and typically 18 bases or greater, which selectively hybridize to genomic DNA which encodes the AgGIF polypeptide of interest. Selective hybridization denotes conditions (e.g., pH, temperature, buffer) which avoid non-specific binding of a nucleotide sequence to the target DNA which is its complement.

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucleic Acid Research,* 9:879, 1981).

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of Alternatively, T cell lines can be used as a convenient source of DNA or RNA. Genetically engineered microorganisms or cell lines containing AgGIF coding sequences may be used as a convenient source of DNA for this purpose.

Antigen-specific T cells which can serve as the source of the AgGIFs and/or the source of genetic material used to produce the AgGIFs used in the methods of the invention may be generated and selected by a number of in vitro techniques that are well-known in the art. A source of T cells may be peripheral blood, lymph nodes, spleens, and other lymphoid organs as well as tissue sites into which T cells have infiltrated such as tumor nodules. The T cell fraction may be separated from other cell types by density gradient centrifugation or cell sorting methods using antibodies to T cell surface markers such as CD2, CD3, CD4, CD8, etc. These methods include, but are not limited to panning, affinity chromatography, flow cytometry, magnetic bead separations. Negative selection procedures may also be employed to enrich for T cells by removing non-T cell populations using antibodies directed to markers not expressed by T cells or utilizing membrane properties of non-T cells such as adhesion to various substrates. Further selection of the T cell subsets of interest may apply the above-mentioned techniques using antibodies to more specific markers such as anti-CD4 and anti-CD8 in selecting for helper and cytotoxic/suppressor T cells, respectively or to markers expressed on T cell subsets such as memory cells.

Antigen-specific T cell lines may be generated in vitro by repetitive stimulation with optimal concentrations of specific antigens in the presence of appropriate irradiated antigen-presenting cells and cytokines. Antigen-presenting cells should be obtained from autologous or MHC-matched sources and they may be macrophages, dendritic cells, Langerhans cells, EBV-transformed B cells or unseparated peripheral blood mononuclear cells. Cytokines may include various interleukins such as interleukin 1, 2, 4, and 6 in natural or recombinant forms. For one such technique, see, for example, Takata, et al., *J. Immunol.* 145:2846–2853, 1990.

Clonal populations of antigen-specific cells may be derived by T cell cloning using limiting dilution cloning methods in the presence of irradiated feeder cells, antigen and cytokines. Alternatively, T cell hybridomas may be generated by fusion of the antigen-specific T cells with fusion partner tumor lines such as BW5147 or BW1100 followed by HAT selection and recloning. Antigen-specific T cells have also been cloned and propagated by the use of monoclonal antibodies to CD3. T cell clones and T cell hybridomas can be generated using cells obtained directly from in vivo sources followed by testing and selection for antigen-specific T cell lines can be secured prior to the cloning and fusion events. T cell clones can be maintained long-term in culture by repetitive stimulation with antigen or anti-CD3 every 7–14 days followed by expansion with cytokines while T cell hybridomas can be grown in the appropriate culture media without periodic antigen stimulation. T cell clones are screened for antigen-specific reactivity (AgGIF) by methods known in the art, including ELISA.

Ts hybridomas which produce AgGIF are preferably the source of cDNA encoding the factor. It is known that antigen-specific T cell factors are derived from the T cell clones that have a certain epitope specificity (Iwata, et al., *J. Immunol.,* 143:3909, 1989; Yamaguchi, et al., *Intl. Immunol.,* 1:337, 1992, Mori, et al., *Intl. Immunol,* 5:833, 1993). The methods to develop GIF-producing Ts populations from antigen-primed mouse spleen cells (Iwata and Ishizaka, *J. Immunol.,* 141:3270, 1988; Ohno, et al., *Intl. Immunol.,* 2:275, 1990) or peripheral blood lymphocytes of allergic individuals (Thomas, et al., *J. Immunol.,* 148:729, 1992), and construction of the GIF-producing Ts hybridomas are known to those of skill in the art. The Ts hybridomas or Ts clones that produce antigen-specific GIF are selected from the GIF-producing hybridomas/clones. The hybridomas/Ts clones are stimulated with antigen-pulsed syngeneic macrophages or by cross-linking of CD3, and culture supernatants are fractionated on antigen-coupled Sepharose or other suitable matrix. Proteins retained in the column are eluted at acid pH, and the presence of GIF bioactivity in the eluate fraction is determined by the methods known to those of skill in the art, such as those described by Iwata and Ishizaka, (*J. Immunol.,* 141:3270, 1988, incorporated herein by reference). The Ts hybridomas or Ts clones which produce antigen-specific GIF upon stimulation are used to clone the gene encoding TCR$\alpha$ chain or AgGIF.

Either cDNA or genomic libraries may be prepared from the DNA fragments generated using techniques well known in the art. The fragments which encode AgGIF may be identified by screening such libraries with a nucleotide probe homologous to a portion of the non-specific GIF and TCR$\alpha$ sequence as described above. In this regard, it should be noted that there is a single constant region gene for TCR$\alpha$ (C$\alpha$) in human and mice. Since the nucleotide sequences encoding the C$\alpha$ for both species are known, DNA probes homologous to the constant region may be synthesized by standard methods in the art and used to isolate from T cells the AgGIF gene or mRNA transcript which can be used to synthesize AgGIF cDNA or to identify appropriate AgGIF sequences in cDNA libraries prepared from such T cells or genomic clones. Alternatively, oligonucleotides specific for the variable region of the desired TCR$\alpha$ chain could be constructed, but these would have to be designed on a case by case basis, depending on the sequence of the variable region. Oligonucleotide probes designed based on the constant region offer an advantage in this regard, since they can be used to "fish out" any AgGIF gene or coding sequence. (See, for example, the techniques described in Maniatis, et al., *Molecular Cloning, A Laboratory Manual,* Cold Spring Harbor Laboratory, N.Y., 1989) In a specific embodiment, by way of example, the complete nucleotide coding sequence for the TCR$\alpha$ chain gene was isolated from T cell hybridoma, 231F1 cells (OVA-specific), depicted in FIGS. 2*a* and *b* and SEQ ID NO: 5.

Alternatively, oligonucleotide probes derived from non-specific GIF and specific TCR$\alpha$ sequences could be used as primers in PCR (polymerase chain reactions) methodologies to generate cDNA or genomic copies of AgGIF sequences which can be directly cloned. For a review of such PCR techniques, see for example, Gelfand, D. H., "PCR Technology, Principles and Applications for DNA Amplification," Ed., H. A. Erlich, Stockton Press, N.Y., 1989; and "Current-Protocols in Molecular Biology," Vol. 2, Ch. 15, Eds. Ausubel, et al., John Wiley & Sons, 1988.

Regardless of the method chosen to identify and clone the AgGIF coding sequence, expression cloning methods may be utilized to substantially reduce the screening effort. Recently, a one step procedure for cloning and expressing antibody genes has been reported (McCafferty et al., *Nature* 348:552–554, 1990; Winter and Milstein, *Nature* 349:293–299, 1991). Based on this technology, AgGIF genes may likewise be cloned directly into a vector at a site adjacent to the coat protein gene of a bacteriophage such as λ or fd. The phage carrying an AgGIF gene expresses the fusion protein on its surface so that columns containing the antigen or an AgGIF-specific antibody (bispecific for non-specific GIF and the constant region of a TCRα chain, or two distinct antibodies) can be used to select and isolate phage particles with binding activity. Transient gene expression systems may also be utilized to identify the correct AgGIF gene. For example, the COS cell system (e.g., Gerard & Gluzmnan, *Mol. Cell. Biol.* 6(12):4570–4577, 1986) may be used. Once a positive clone is selected, bioactivity of the gene product (AgGIF) can be assayed for antigen-specificity by methods known in the art and as described herein.

Due to the degeneracy of the nucleotide coding sequences, other DNA sequences which encode analogous amino acid sequences for any known AgGIF gene may be used in the practice of the present invention for the cloning and expression of a AgGIF. Such alterations include deletions, additions or substitutions of different nucleotide residues resulting in a sequence that encodes the same or a functionally equivalent gene product. The gene product may contain deletions, additions or substitutions of amino acid residues within the sequence, which result in a silent change thus producing a bioactive product. Such amino acid substitutions may be made on the basis of similarity in polarity, charge, solubility, hydrophobicity, hydrophilicity, the amphipathic nature of the residues involved and SH groups. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. One may also substitute appropriate cysteine residues with alanine/serine to remove sulfhydryl (SH) groups, which may affect conformation and thus bioactivity of a protein.

Regardless of the method used to produce such AgGIFs, the antigen binding capability and immunoregulatory activity of the molecule should be evaluated. For example, the ability of the AgGIF to directly bind to an antigen of interest may be evaluated by modified immunoassay techniques including, but not limited to ELISA (enzyme-linked immunosorbent assay), immunoprecipitation, Western blots, or radioimmunoassays in which the AgGIF is substituted for the antibody normally used in these assay systems. Examples of these assays are illustrated in the EXAMPLES section which follows.

The immunoregulatory capability of the antigen-binding AgGIF may be evaluated using any assay system which allows the detection of an immune response in an antigen-specific fashion. For example, the plaque forming cell (PFC) assay as described and exemplified herein may be utilized to identify AgGIFs that suppress immune responses directed toward a particular antigen. When spleen cells are cultured in the presence of a highly immunogenic carrier, such as sheep red blood cells (SRBC), an immune response occurs which results in the generation of plaque forming cells. The number of PFC generated per culture is assessed by mixing the cultured spleen cells with SRBC (or appropriate lysable carrier) and complement, and culturing the mixture as a monolayer. Cells surrounded by a clear plaque (e.g., of lysed red cells) are counted as PFCs. Inhibition of PFC generation in the spleen cell culture, i.e., a reduction in the number of PFC/culture, indicates suppression of the immune response. In order to test AgGIFs for suppressive activity, and to ensure that the suppression is antigen specific, the PFC assay may be conducted as follows: the antigen of interest is coupled to SRBC (Ag-SRBC) and added to spleen cells from unimmunized mice. The immunoregulatory effect of AgGIF specific for the antigen is assessed by adding the AgGIF to be tested to the culture in the presence of an accessory component described below (i.e., the accessory component should be added to the culture prior to or simultaneously with the AgGIF to be tested). Control cultures receive the AgGIF or may involve the use of an irrelevant antigen. Following culture, the number of PFC/culture is assessed for each condition. An inhibition of PFC generation in the test cultures, as compared to that observed in the controls, indicates that the AgGIF tested suppresses, in an antigen-specific manner, the immune response which is normally generated in the culture system.

The antigen-specificity of monoclonal T cell populations can be assessed in in vitro assays measuring the proliferation and/or lymphokine production of these cells in response to antigen. Phenotype of the T cells may be confirmed by staining with antibodies to various T cell markers. In addition, ELISA can be used to test T cells for antigen-specificity.

Such antigen-specific T cells may secrete AgGIFs constitutively or they may require activation signals for the release of AgGIF. Preferably, the antigen-specific T cells may be used as the source of genetic material required to produce the AgGIF polypeptide by recombinant DNA and/or chemical synthetic techniques. Using this approach, certain antigen-specific T cells which may not secrete naturally-occurring AgGIFs can serve as a source of genetic material for the AgGIF to be used in accordance with the invention.

In another embodiment, the invention provides a method for the recombinant production of substantially pure biologically active AgGIF comprising culturing a host cell transformed with a polynucleotide sequence encoding a fusion polypeptide having a sequence with the formula $R_1$–$R_2$, wherein $R_1$ is non-specific GIF and $R_2$ is a TCRα chain, under conditions which allow expression of the polynucleotide sequence, and isolating substantially pure AgGIF. Preferably the AgGIF is either murine or human.

The term "substantially pure" as used herein refers to a polypeptide which is substantially free of other proteins, lipids, carbohydrates or other materials with which it is naturally associated. One skilled in the art can purify the polypeptide using standard techniques for protein purification, such as affinity chromatography using a monoclonal antibody which binds an epitope of non-specific GIF and an epitope of TCRα constant region, as previously described herein. The substantially pure polypeptide will yield a single major band of approximately 55 kD on a reducing SDS-polyacrylamide gel. The purity of the polypeptide can also be determined by amino-terminal amino acid sequence analysis. The polypeptide includes functional fragments of the polypeptide, as long as the activity of the polypeptide remains. Smaller peptides containing the biological activity of polypeptide are included in the invention.

In order to express a biologically active AgGIF, the nucleotide sequence coding for AgGIF is inserted into an appropriate expression vector, i.e., a vector which contains the necessary elements for the transcription and translation of the inserted coding sequence. Modified versions of the AgGIF coding sequence could be engineered to enhance stability, production, purification or yield of the expressed product. For example, the expression of a fusion protein or a cleavable fusion protein comprising AgGIF and a heterologous protein may be engineered. Such a fusion protein may be readily isolated by affinity chromatography; e.g. by immobilization on a column specific for the heterologous protein. Where a cleavage site is engineered between the AgGIF moiety and the heterologous protein, the AgGIF can be released from the chromatographic column by treatment with an appropriate enzyme or agent that disrupts the cleavage site (e.g., see Booth, et al., *Immunol Lett.*, 19:65–70, 1988; and Gardella, et al., *J. Biol. Chem.*, 265:15854–15859, 1990).

cDNA encoding TCRα can be transfected into a Ts cell which expresses GIF in order to produce biologically active AgGIF (see Example 4). Alternatively, both GIF and TCRα polynucleotides can be co-transfected to a cell, producing AgGIF. In addition, it may be desirable to also transfect a TCRβ chain cDNA in the same host cell.

Methods which are well known to those skilled in the art can be used to construct expression vectors containing the AgGIF coding sequence and appropriate transcriptional/translational control signals. These methods include in vitro recombinant DNA techniques, synthetic techniques and in vivo recombination/genetic recombination. (See, for example, the techniques described in Maniatis, et al., *Molecular Cloning A Laboratory Manual,* Cold Spring Harbor Laboratory, N.Y., 1989).

Transformation of a host cell with recombinant DNA may be carried out by conventional techniques as are well known to those skilled in the art. Where the host is prokaryotic, such as *E. coli,* competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the fusion polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors,* Cold Spring Harbor Laboratory, Gluzman ed., 1982). Preferably, a eukaryotic host is utilized as the host cell as described herein.

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies or antigen.

A variety of host-expression vector systems may be utilized to express AgGIF coding sequence. These include but are not limited to microorganisms such as bacteria transformed with recombinant bacteriophage DNA, plasmid DNA or cosmid DNA expression vectors containing a AgGIF coding sequence; yeast transformed with recombinant yeast expression vectors containing the AgGIF coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a AgGIF coding sequence; insect cell systems infected with recombinant virus expression vectors (e.g., baculovirus) containing a AgGIF coding sequence; or animal cell systems infected with recombinant virus expression vectors (e.g., retroviruses, adenovirus, vaccinia virus) containing a AgGIF coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see e.g., Bitter, et al., *Methods in Enzymology* 153:516–544, 1987). For example, when cloning in bacterial systems, inducible promoters such as pL of bacteriophage λ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted AgGIF coding sequence.

In bacterial systems a number of expression vectors may be advantageously selected depending upon the use intended for the AgGIF expressed. For example, when large quantities of AgGIF are to be produced, vectors which direct the expression of high levels of fusion protein products that are readily purified may be desirable. Those which are engineered to contain a cleavage site to aid in recovering AgGIF are preferred. Such vectors include but are not limited to the *E coli* expression vector pUR278 (Ruther et al., *EMBO J.* 2:1791, 1983), in which the An AgGIF coding sequence may be ligated into the vector in frame with the lac Z coding region so that a hybrid AgGIF-lac Z protein is produced; pIN vectors (Inouye & Inouye, *Nucleic acids Res.* 13:3101–3109, 1985; Van Heeke & Schuster, *J. Biol. Chem.* 264:5503–5509, 1989); and the like.

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., Expression and Secretion Vectors for Yeast, in Methods in Enzymology, Eds. Wu & Grossman, 31987, Acad. Press, N.Y., Vol. 153, pp. 516–544, 1987; Glover, DNA Cloning, Vol. II, IRL Press, Wash., D.C., Ch. 3, 1986; and Bitter, Heterologous Gene Expression in Yeast, Methods in Enzymology, Eds. Berger & Kimmel, Acad. Press, N.Y., Vol. 152, pp. 673–684, 1987; and The Molecular Biology of the Yeast Saccharomyces, Eds. Strathern et al., Cold Spring Harbor Press, Vols. I and II, 1982. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, IRL Press, Wash., D.C., 1986). Alternatively, vectors may be used which promote integration of foreign DNA sequences into the yeast chromosome.

In cases where plant expression vectors are used, the expression of a AgGIF coding sequence may be driven by any of a number of promoters. For example, viral promoters such as the 35S RNA and 19S RNA promoters of CaMV (Brisson, et al., *Nature* 310:511–514, 1984), or the coat protein promoter to TMV (Takamatsu, et al., *EMBO J.* 6:307–311, 1987) may be used; alternatively, plant promoters such as the small subunit of RUBISCO (Coruzzi, et al., 1984, *EMBO J.* 3:1671–1680; Broglie, et al., *Science* 224:838–843, 1984); or heat shock promoters, e.g., soybean hsp17.5-E or hsp17.3-B (Gurley, et al., *Mol. Cell. Biol.* 6:559–565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, *Methods for Plant Molecular Biology*, Academic Press, NY, Section VIII, pp. 421–463, 1988; and Grierson & Corey, *Plant Molecular Biology*, 2d Ed., (Coruzzi, et al., 1984, EMBO J. 3:1671–1680; Broglie, et al., *Science* 224:838–843, 1984); Blackie, London, Ch. 7–9, 1988.

An alternative expression system which could be used to express AgGIF is an insect system. In one such system, *Autographa californica* nuclear polyhedrosis virus (AcNPV) is used as a vector to express foreign genes. The virus grows in *Spodoptera frugiperda* cells. The AgGIF coding sequence may be cloned into non-essential regions (for example, the polyhedrin gene) of the virus and placed under control of an AcNPV promoter (for example the polyhedrin promoter). Successful insertion of the AgGIF coding sequence will result in inactivation of the polyhedrin gene and production of non-occluded recombinant virus (i e., virus lacking the proteinaceous coat coded for by the polyhedrin gene). These recombinant viruses are then used to infect *Spodoptera frugiperda* cells in which the inserted gene is expressed, see Smith, et al., *J. Viol.* 46:584, 1983; Smith, U.S. Pat. No. 4,215,051.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used as host cells for the expression of AgGIF. Mammalian cell lines are preferred. Such host cell lines may include but are not limited to CHO, VERO, BHK, HeLa, COS, MDCK, -293, and WI38 and Ts hybridomas (which express GIF). For example, a human TCRα polynucleotide can be transfected into a murine or human Ts cell which expresses GIF, and bioactive human AgGIF will be expressed (EXAMPLE 4).

Mammalian cell systems which utilize recombinant viruses or viral elements to direct expression may be engineered. For example, when using adenovirus expression vectors, the AgGIF coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the AgGIF in infected hosts (e.g., see Logan & Shenk, *Proc. Natl. Acad. Sci. USA*, 81: 3655–3659, 1984). Alternatively, the vaccinia virus 7.5K promoter may be used. (e.g., see, Mackett, et al., *Proc. Natl. Acad. Sci. USA*, 79: 7415–7419, 1982; Mackett, et al., *J Virol.* 49: 857–864, 1984; Panicali, et al., *Proc. Natl. Acad. Sci. USA* 79: 4927–4931, 1982). Of particular interest are vectors based on bovine papilloma virus which have the ability to replicate as extrachromosomal elements (Sarver, et al., *Mol. Cell. Biol.* 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the AgGIF gene in host cells (Cone & Mulligan,, *Proc. Natl. Acad. Sci. USA*, 81:6349–6353, 1984). High level expression may also be achieved using inducible promoters, including, but not limited to, the metallo-thionine IIA promoter and heat shock promoters.

For long-term, high-yield production of recombinant proteins, stable expression is preferred. Rather than using expression vectors which contain viral origins of replication, host cells can be transformed with the AgGIF cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., *Cell*, 11: 223, 1977), hypoxanthine-guanine phosphoribosyltransferase (Szybalska & Szybalski, *Proc. Natl. Acad. Sci. USA*, 48:2026, 1962), and adenine phosphoribosyltransferase (Lowy, et al., *Cell*, 22: 817, 1980) genes can be employed in tk$^-$, hgprt$^-$, or aprt$^-$ cells respectively. Also, antimetabolite resistance can be used as the basis of selection for dhfr, which confers resistance to methotrexate (Wigler, et al., *Proc. Natl. Acad. Sci. USA*, 77: 3567, 1980; O'Hare, et al., *Proc. Natl. Acad. Sci. USA*, 8: 1527, 1981); gpt, which confers resistance to mycophenolic acid (Mulligan & Berg, *Proc. Natl. Acad. Sci. USA*, 78: 2072, 1981; neo, which confers resistance to the aminoglycoside G-418 (Colberre-Garapin, et al., *J. Mol. Biol.*, 150:1, 1981); and hygro, which confers resistance to hygromycin (Santerre, et al., *Gene*, 30: 147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA*, 85:8047, 1988); and ODC (ornithine decarboxylase) which confers resistance to the omithine decarboxylase inhibitor, 2-(difluoromethyl)-DL-ornithine, DFMO (McConlogue L., In: *Current Communications in Molecular Biology*, Cold Spring Harbor Laboratory, ed., 1987).

The expression of AgGIF protein product by genetically-engineered cells can be assessed immunologically, for example by Western blots, immunoassays such as radioimmuno-precipitation, enzyme-linked immunoassays and the like. The ultimate test of the success of the expression system, however, involves the production of biologically active AgGIF gene product. Where the host cell secretes the gene product, the cell free media obtained from the cultured transfectant host cell may be assayed for AgGIF or its immunoregulatory activity. Where the gene product is not secreted, cell lysates may be assayed for such activity. In either case, a number of assays can be used to assess AgGIF activity, including but not limited to assays measuring the ability of the expressed AgGIF to bind antigen, or the ability to switch the T cell hybridoma from the formation of glycosylated IgE-binding factor to the formation of unglycosylated IgE-binding factor (EXAMPLE 1), and assays to evaluate its immunologic function, such as a PFC assay.

Alternatively, antigen-specific GIF (the 55 kDa peptide having GIF activity) may be prepared as a fusion protein of bioactive GIF and TCRα chain. The 13 kDa GIF polypeptide sequence is produced by various cell line cells, but only the polypeptide produced by Ts cells is biologically active (Liu, et al., *Proc. Natl. Acad. Sci. USA,* 91:11227, 1994). Stable transfectants of human GIF cDNA in murine Ts cells produce bioactive human GIF as described in Liu, et al., supra Transfection of a chimeric cDNA encoding a fusion protein consisting of the N-terminal region of procalcitonin precursor and human GIF into BMT10 cells or COS cells results in the secretion of bioactive GIF, 13 kDa. This human GIF polypeptide can be affinity-purified by using anti-GIF coupled to Affigel, for example.

A bacterial fusion expression system with calmodulin or other carriers as a fusion partner for the production of soluble form TCRα chain can also be utilized. The system provides a high level of expression of the calmodulin-TCRα fusion protein in the soluble fraction of the cell lysate, and facilitates rapid purification of the fusion protein, based on the high affinity of the calmodulin portion of the protein to phenyl-Sepharose. Recombinant TCRα chain can be recovered by digestion of the fusion protein with thrombin, which recognizes a linker sequence between calmodulin portion and TCRα chain. By this method, TCRα chain consisting of Vα, Jα, Cα extracellular region is obtained. The same method is also useful for the production of soluble form TCRβ chain as well. Although SH groups in the bioactive GIF molecule are blocked, mild reduction of a mixture of recombinant GIF peptide and TCRα chain, followed by treatment of the mixture with protein disulfide isomerase results in the formation of interchain disulfide linkage between the TCRα chain and GIF. GIF peptide may be conjugated to TCRα chain using cementoin, containing 5 cycles of VKGLDP sequence which can be conjugated to two independent peptides in the presence of transglutaminase, for example. Other carriers and fusion partners having cleavage sites useful for producing fusion partners will be known to those of skill in the art.

In yet another embodiment, the present invention provides a method for isolating substantially pure AgGIF polypeptide comprising activating a suppressor T cell, wherein activation induces gene expression in the T cell, independently contacting suppressor T cell expression products with an antibody which binds to non-specific GIF polypeptide and an antibody which binds to TCRα polypeptide, and isolating the polypeptide which binds to both GIF antibody and TCRα antibody.

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual,* Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the AgGIF polypeptide or the TCRα constant region as described in the invention, can be prepared using an intact polypeptide or fragments containing small peptides of interest as the immunizing antigen. The polypeptide such as SEQ ID NO:2 (GIF) or a peptide containing an epitope from SEQ ID NO:2, or the constant region from the TCRα chain used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., mouse, rat, goat, rabbit).

Once a clone that produces high levels of biologically active AgGIF is identified, the clone may be expanded and used to produce large amounts of the protein which may be purified using techniques well-known in the art including, but not limited to immuno-affinity purification, chromatographic methods including high performance liquid chromatography and the like. Where the protein is secreted by the cultured cells, AgGIF may be readily recovered from the culture medium.

Methods for purifying AgGIF from crude culture media of T cells may be adapted for purification of the cloned, expressed product. For example, AgGIF from 231F1 cells, used in the examples, infra, can be purified from the crude culture media of T cells by ammonium sulfate precipitation followed by affinity chromatography (Zheng, et al., *J. Immunol.,* 140:1351–1358, 1988; Bissonnette, et al., *J. Immunol.,* 146:2898–2907, 1991). Purified monoclonal antibodies specific for a commonly shared determinant on all AgGIFs (e.g., GIF and TCRα constant region) or an antigen or a fragment containing a specific antigenic epitope thereof can be coupled to cyanogen bromide-activated Sepharose 4B (Pharmacia) or Affigel 10 (BioRad) and used for affinity chromatography. Alternatively, antibodies made to products of different Vα gene families may also be used if it is known which specific Vα gene segment encodes the α chain protein in question. In addition, antibodies may be raised to the variable region of a specific AgGIF and used in the purification of the α chain from a mixture of other irrelevant AgGIFs. In this case, a specific AgGIF may be isolated even from the crude media of bulk culture T cells if sufficient quantity of the protein is present.

Where the AgGIF coding sequence is engineered to encode a cleavable fusion protein, the purification of AgGIF may be readily accomplished using affinity purification techniques. For example, a protease factor Xa cleavage recognition sequence can be engineered between the carboxyl terminus of AgGIF and a maltose binding protein. The resulting fusion protein can be readily purified using a column conjugated with amylose to which the maltose binding protein binds. The AgGIF fusion protein is then eluted from the column with maltose containing buffer followed by treatment with Factor Xa. The cleaved AgGIF is further purified by passage through a second amylose column to remove the maltose binding protein (New England Biolabs, Beverly, Mass.). Using this aspect of the invention, any cleavage site or enzyme cleavage substrate may be engineered between the AgGIF sequence and a second peptide or protein that has a binding partner which could be used for purification, e.g., any antigen for which an immunoaffinity column can be prepared.

Once a specific AgGIF gene has been molecularly cloned and its DNA sequence determined, its protein product may be produced by a number of methods in addition to those described supra. For example, solid phase chemical synthetic techniques can be used to produce a AgGIF in whole or in part based on an amino acid sequence deduced from the DNA sequence (see Creighton, *Proteins Structures and Molecular Principles,* W.H. Freeman and Co., N.Y. pp. 50–60, 1983). This approach is particularly useful in generating small portions of proteins that correspond to the active site of a molecule. In the case of a AgGIF which binds antigen, it is highly likely that the variable region in the amino-terminal end of the protein encoded by the V and J gene segments is important to antigen-binding. Therefore, synthetic peptides corresponding to the variable region of the α chain may be produced. In addition, a larger peptide containing a specific portion of an α chain constant region may also be synthesized if, for example, that region is known to be important for its interaction with accessory factors in achieving a full immuno-regulatory response.

Another method of producing AgGIF based on its cloned DNA sequence is by transcription and translation of its gene in an in vitro cell free system. In a particular embodiment by way of example herein the 231F1 AgGIF gene is in vitro transcribed and translated and its product is shown to be a protein of about 55,000 dalton molecular weight by reducing SDS-PAGE. This protein corresponds to an unglycosylated AgGIF polypeptide chain. Although such a cell free in vitro system is not designed for large scale protein production, the advantage of this approach is to provide a method for definitively demonstrating the contribution of a specific AgGIF in a specific immunological reaction in the absence of the synthesis of other proteins.

The antigen-specific immunoregulatory activity of a AgGIF provides for a wide variety of uses in vivo in human or animal subjects and in vitro. Any AgGIF or fragments and derivatives thereof, which are capable of binding to the antigen and which exhibit immunoregulatory activities as assayed in vitro may be used in the practice of the method of the invention. The AgGIFs which are capable of binding to the antigen and which suppress the immune response that would normally be generated against the antigen may be especially useful in the down-regulation of antigen-specific immune responses such as hypersensitivity reactions, transplantation rejections, and autoimmune disorders.

The invention therefore also provides a method of suppressing a human immune response to an antigen comprising administering to the human an immunosuppressive amount of antigen-specific GIF (AgGIF) and suppressing the immune response. The term "suppressing" or "suppressive" denotes a lessening of the detrimental effect of the undesirable immune response in the human receiving therapy. The term "immunosuppressive amount" means that the amount of human AgGIF used is of sufficient quantity to suppress the cause of disease or symptoms due to the undesirable immune response. The method may further include administration of a conjugate of the 55 kDa peptide with the TCRβ chain. TCRβ may be conjugated with AgGIF by methods known to those of skill in the art, for example by chemical conjugation or conjugation via disulfide bond formation.

The dosage ranges for the administration of the AgGIF of the invention are those large enough to produce the desired effect in which the symptoms of the immune response show some degree of suppression. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary from about 0.001 mg/kg/dose to about 2 mg/kg/dose, preferably about 0.001 mg/kg/dose to about 0.2 mg/kg/dose, in one or more dose administrations daily, for one or several days.

The AgGIF of the invention can be administered parenterally by injection or by gradual perfusion over time. The human AgGIF of the invention can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention also relates to a method for preparing a medicament or pharmaceutical composition comprising the AgGIF of the invention, the medicament being used for therapy of an undesirable immune response to an antigen wherein the antigen is capable of being bound by the AgGIF of the invention. Preferably, the AgGIF is human AgGIF.

The antigen-binding AgGIFs that demonstrate antigen-specific immunosuppression may be used in the treatment of conditions in which immune reactions are deleterious and suppression of such responses in an antigen-specific manner is desirable. These disorders which may be treated in accordance with the invention include but are not limited to hypersensitivity (types I–IV), autoimmune disease as well as graft rejection responses after organ and tissue transplantations.

Hypersensitivity reactions are commonly classified into four groups. Type I reactions are immediate-type hypersensitivity which result from mast cell degranulation triggered by antigen-specific IgE. Examples of type I diseases include most common allergies caused by substances such as plant pollens, mold spores, insect parts, animal danders, bee and snake venom, industrial dusts, house dusts, food products, chemicals and drugs. Type II reactions are caused by the action of specific antibodies, usually IgG and IgM, on target cells leading to cellular destruction. Examples of type II diseases include transfusion reactions, erythroblastosis fetalis, autoimmune hemolytic anemia, myasthenia gravis and Grave's disease. Type III reactions are caused by antigen-antibody complex formations and the subsequent activation of antibody effector mechanisms. Examples of type III diseases include immune complex glomerulonephritis, Goodpasture's syndrome and certain forms of arthritis. Type IV reactions are cell-mediated reactions involving T cells, macrophages, fibroblasts and other cell types. These are also referred to as delayed-type hypersensitivity. Allergic contact dermatitis is a typical example of this category.

Autoimmune disorders refer to a group of diseases that are caused by reactions of the immune system to self antigens leading to tissue destruction. These responses may be mediated by antibodies, auto-reactive T cells or both. Many of these conditions overlap with those described under hypersensitivity above. Some important autoimmune diseases include diabetes, autoimmune thyroiditis, multiple sclerosis, rheumatoid arthritis, systemic lupus erythematosis, and myasthenia gravis.

Basic understanding of the MHC has led to technical advances in tissue typing which, in turn, have substantially improved the rate of success in organ and tissue transplantation. Some of the commonly performed transplantation surgery today includes organs and tissues such as kidneys, hearts, livers, skin, pancreatic islets and bone marrow. However, in situations where the donors and recipients are not genetically identical, graft rejections can still occur.

For all of the above-identified conditions, including but not limited to the specific diseases mentioned, a down-regulation of adverse immune reactions is beneficial to the host. In this regard, an AgGIF may be used to specifically suppress an immune response mediated by T cells, antibodies or both while retaining all other normal immune functions. For example, experimental allergic encephalomyelitis (EAE) is an animal model for multiple sclerosis in man which can be induced in mice by the administration of purified myelin basic protein. $T_H$ have been shown to play a critical role in the pathogenesis of the disease (Wraith, et al., Cell, 57:709–715, 1989). The number of antigenic determinants recognized by auto-reactive T cells in a given mouse strain are limited. Furthermore, the Vα and Vβ gene segments used for the construction of autoimmune TCR is equally restricted so that the majority of the T cell response to the small number of encephalitogenic epitopes has an identical TCR. Antibodies to TCR determinants have been successfully used to deplete Ag T cells in vivo leading to protection from disease. (Owhashi and Heber-Katz, J Exp. Med, 168:2153–2164, 1988). For the practice of the present invention, a AgGIF gene may be isolated from such auto-reactive T cells, expressed in an appropriate host cell and tested for its ability to suppress the antigen-specific immune responses in vitro and in vivo. The use of AgGIFs for this purpose is particularly important in light of the recent findings that in certain human diseases such as multiple sclerosis and myasthenia gravis, autoimmune T cells have been detected and they appear to similarly have a restricted usage of certain Vα and Vβ alleles (Oksenberg, et al., Proc. Natl. Acad. Sci. USA, 86:988–992, 1989).

In accordance with the invention, the foregoing conditions may be treated by administering to the patient an effective dose of AgGIF specific for the relevant antigen which suppresses the immune response generated against that antigen. The AgGIFs selected for use may be evaluated by an immunoregulatory assay in vitro, such as the PFC assays described herein. The AgGIF may be administered in a variety of ways, including but not limited to injection, infusion, parenterally, and orally. AgGIF and its related derivatives, analogs e.g., peptides derived from the variable region, may be used as the sole active agent, or with other compounds. Such compositions may be administered with a physiologically acceptable carrier, including phosphate buffered saline, saline and sterilized water. Alternatively, liposomes may be used to deliver the AgGIF. In this regard, the liposome may be conjugated to antibodies that recognize and bind to cell specific antigens, thereby providing a means for "targeting" the AgGIF compositions.

An effective dose is the amount required to suppress the immune response which would have been generated against the relevant antigen in vivo. The amount of AgGIF employed will vary with the manner of administration, the use of other active compounds, and the like. Generally a dose which will result in circulating serum levels of 0.1 μg to 100 μg/ml may be utilized. The most effective concentration for suppressing antigen-specific responses may be determined in vitro by adding various concentrations of AgGIF to an in vitro assay such as the PFC assays described herein and known by those of skill in the art, and monitoring the level of inhibition achieved.

The following examples are intended to illustrate but not limit the invention. While they are typical of those that might be used, other procedures known to those skilled in the art may alternatively be used.

EXAMPLE 1

MATERIALS AND METHODS

Cell Lines

The OVA-specific suppressor T cells (Ts) hybridoma 231F1 cells (Jardieu, et al., J. Immunol., 138:1494, 1987), bee venom phospholipase $A_2$ ($PLA_2$)-specific Ts hybridoma 3B3 cells (Mori, et al., Int. Immunol., 5:833, 1993), a T cell line 175.2 which contains TCRβ chain mRNA and CD3-mRNA but no TCRα chain cDNA (Glaichenhans, et al., J. Immunol., 146:2095, 1991) were used. Both the 231F1 cells and 3B3 cells expressed TCR on the cell surface, as determined by immunofluorescence with monoclonal anti-TCRβ chain and anti-CD3, but the 175.2 cells were not stained by either antibody.

Antigens and Antibodies

Crystalline ovalbumin was purchased from Nutritional Biochem. and bee venom phospholipase $A_2$ was purchased from Sigma Chemical Co. (St. Louis, Mo.). The antigen was coupled to CL Sepharose 4B at 1–3 mg protein per ml of the gel. $PLA_2$ was treated with CNBr as previously described (Mori, et al., supra) anti-mouse CD3 (145-2C11), (Lee, et al., Pro. Natl. Acad. Sci., U.S.A., 84:1374, 1987), anti-TCRα chain (H28-710), (Beker, et al., Cell, 87:911, 1989) and anti-TCRβ chain (H57-597) (Kubo, et al., J. Immunol, 142:2736, 1989) mAB and polyclonal rabbit anti-GIF antibodies, (Mikayama, et al., *Proc. Natl. Acad. Sci. USA*, 90:10056, 1993) were previously described. All of the monoclonal antibodies (mAbs) were purified by absorption of culture supernatant or anti-serum with Protein A Sepharose, and IgG retained in the column was recovered by elution with 0.1M glycine HCl buffer, pH 3.0. The mAb H28-710, H57-597 or the IgG fraction of rabbit anti-GIF antiserum was coupled to Affigel 10. Two to 4 mgs of the mAb or 5 mg of the anti-GIF were coupled to 1 ml gel. Normal rabbit IgG (RGG) was coupled to Affigel 10 at 5 mg protein per ml gel.

PCR and DNA Sequencing

Poly (A)+ RNA was isolated from 231F1 cells by using a FastTrack mRNA isolation kit (Invitrogen) and reverse-transcribed into cDNA. Double stranded cDNAs were generated by using cDNA synthesis system (Gibco BRL), and circularized with T4 ligase (Inaba, et al., *Internat. Immunol.*, 3:1053, 1991). PCR primers for TCRα cDNA cloning were synthesized. The nucleotide sequences of the primers were: 5'-CGAGGATCTTTTAACTGGTACACA-3' (nucleotide 47 to 24 in Cα) (SEQ ID NO:7); 5'-GTAGCGGGATTTAACCTGCTCATG-3' (366 to 389 in Cα) (SEQ ID NO:8); 5'-CGACAACTGTGCAGTGGTTCCTAC-3' (146 to 169 in FIG. 2a) (SEQ ID NO:9); 5'-AGGAACAAAGGAGAATGGGAGG-3' (213 to 234 in FIG. 2a) (SEQ ID NO:10); 5'-TCAACTGGACCACAGGCCTCAGC-3' (804 to 784 in FIG. 2a) (SEQ ID NO:11), respectively. PCR reaction was carried out at 95° C. for 1 min for denaturation, at 55° C. for 2 min for annealing and at 72° C. for 2 min for extension. Amplified DNA was isolated and inserted into the TA cloning vector PCRII (Invitrogen). DNA sequencing was carried out by the standard dideoxy method with a sequence kit (United States Biochemical).

Construction of Expression Vector and Stable Transfection

Mammalian expression vector pEFneo was described previously (Liu, et al., *Proc. Natl. Acad. Sci., USA*, 91:11227, 1994). Full length cDNA encoding TCRα chain was amplified by PCR using two primers corresponding to the 5' end of TCRα cDNA with XbaI site and 3' end of the cDNA with NotI site, and the cDNA was inserted into pEFneo. The TCRα-tag gene was made by PCR using the 5' primer described above and 3' primer encoding 3' end of TCRα, a linker sequence for enterokinase, tag domain for six histidine residues and NotI site, and was inserted in the same vector. Transfection was carried out by electroporation (Bio-Rad) at 200 V, 960 µF. Stable transfectants were selected by G418 resistance (0.5 mg/ml). The expression of TCRα mRNA was evaluated by Northern blot hybridization using [$^{32}$P] labeled Vα11.3-specific probe.

Stimulation of Hybridoma Cells and Stable Transfectants

For antigen stimulation of the 231F1 cells and 3B3 cells, the T cell hybridomas (1×10$^6$ cells/ml) suspended in DMEM with 10% Nu-serum were co-cultured with A20.3 cells (2×10$^5$ cell/ml) which had been pulsed with 100 µg/ml OVA (Jardieu, et al., supra) or 30 µg/ml CNBr-treated PLA$_2$ (Mori, et al., supra). After 24 hr culture, supernatants were recovered. To stimulate the hybridoma cells or stable transfectants by cross-linking of CD3, the cells were treated with 5 µg/ml anti-CD3 on ice for 30 min. The cells were washed, resuspended in serum free DMEM and the cell suspension containing 10$^6$/ml cells were cultured in tissue culture flasks which had been coated with protein A (Iwata, et al., *J. Immunol.*, 143:3909, 1989). Culture supernatants were recovered after 24 hr incubation.

Fractionation of Culture Supernatants

Culture supernatants or cytosolic fraction of a cell line cells were fractionated on an appropriate immunosorbent. Unless otherwise described, the culture supernatant was concentrated 10 to 50 fold by ultrafiltration, and the samples were mixed overnight with a ⅓–⅕ volume of RGG-coupled Affigel 10. The suspension was packed into a column, and the flow through fraction together with washing was applied to a 2–3 ml immunosorbent column. The preparation was circulated through the column overnight, which was then washed with 40–50 column volumes of PBS. Proteins retained in the immunosorbent column were recovered by elution with 3 column volumes of 0.1M glycine HCl buffer, pH 3.0. Recombinant peptides bearing His-tag were purified using Ni-NTA agarose (Qiagen). Concentrated culture supernatants were dialyzed against 50 mM sodium phosphate buffer, pH 8, at 4° C., and NaCl was added at a final concentration of 300 mM. The samples were gently mixed at 4° C. for 30 +lmin with one-tenth volume of Ni-NTA agarose and the suspension was packed into a column. After washing the 40 column volumes of the phosphate buffer, containing 1 mM Imidazole, proteins retained in the column were eluted with the phosphate buffer containing 100 mM Imidazole.

SDS-PAGE and Immunoblotting

Affinity-purified preparations were analyzed by SDS-PAGE in a 15% polyacrylamide gel under reducing conditions. In some experiments, the samples were analyzed along with *E. coli*-derived recombinant human GIF, which was supplied by T. Mikayama (Kirin Brewery Co., Maebashi, Japan). Proteins in the gel were transferred to PVDF membrane, and immunoblotting was carried out with the enhanced chemiluminescence Western blot detection system (Amersham). The IgG fraction of polyclonal rabbit anti-GIF and the mAb H28-710, were employed for the detection of a peptide with the GIF epitope and that with TCRα chain determinant, respectively.

Detection of GIF Bioactivity

The activity was detected by its ability to switch the mouse T cell hybridoma 12H5 cells from the formation of glycosylated IgE-binding factor (IgE-BF) to the formation of unglycosylated IgE-BF. Detailed procedures for the assay have been described (Iwata, M. and Ishizaka, K., *J. Immunol.*, 141:3270, 1988). Briefly, the 12H5 cells were cultured with mouse IgE in the presence of serial two fold dilutions of a sample to be tested, and IgE-BF in culture filtrates were fractionated on lentil lectin Sepharose. When the 12H5 cells were cultured with IgE alone, essentially all IgE-BF formed by the cells bound to lentil lectin Sepharose, and was recovered by elution with a methyl mannoside. When a sufficient amount of GIF was added to the 12H5 culture, however, most of the IgE-BF was not retained in lentil lectin Sepharose, and was recovered in the flow through fraction. GIF titer of a sample represents a maximum dilution of the sample which is the nature of Ige-BF formed by the 12H5 cells.

EXAMPLE 2

IDENTIFICATION OF THE 55 KD PEPTIDE IN ANTIGEN-SPECIFIC GIF

The following experiment describes the identification of antigen-specific GIF. The OVA-specific Ts hybridoma 231F1 cells were co-cultured with OVA-pulsed A20.3 cells for 24 hr. After concentration of culture supernatants by ultrafiltration, the concentrated culture supernatant was fractionated on OVA-coupled Sepharose. Distribution of GIF bioactivity between the flow through fraction and acid eluate fraction showed that 80 to 90% of the GIF bioactivity in the original culture supernatant was retained in the immunosorbent column and was recovered in acid eluates. Thus, the acid eluate was analyzed by SDS-PAGE, followed by immunoblotting with polyclonal anti-GIF. The major band which bound anti-GIF represented a 55 kDa peptide. A similar experiment was carried out with culture supernatant of antigen-stimulated $PLA_2$-specific Ts hybridoma 3B3 cells.

FIG. 1 shows analysis of antigen-specific GIF from Ts hybridomas. FIG. 1A shows the results of $PLA_2$-specific GIF obtained by stimulation of 3B3 cells with antigen-pulsed APC, and affinity purified using $PLA_2$-coupled Sepharose (lane 2). E coli derived recombinant human GIF was applied to lane 1. They were subjected to SDS-PAGE under reducing conditions, followed by immunoblotting with anti-GIF. In FIG. 1B, OVA-specific GIF was affinity purified from anti-CD3-stimulated 231F1 cells using H28-710-coupled Affigel. The eluate fraction (lane 1), having GIF titer of 1:80 was further fractionated on OVA-Sepharose. Acid eluate (lane 2) and flow-through (Eff, lane 3) were analyzed by SDS-PAGE and immunoblotting with anti-GIF. FIG. 1C shows the same fractions analyzed by immunoblotting with H28-710.

As shown in FIG. 1A analysis of the eluate from antigen-coupled sepharose by SDS-PAGE under reducing conditions and Western blot with anti-GIF showed a single band of 55 kDa. Similar results were obtained when OVA-specific Ts hybridoma 231F1 cells were stimulated with OVA pulsed APCs and OVA-specific GIF was purified using OVA-sepharose. Identification of the 55 kDa peptide in both the OVA-specific GIF preparation and $PLA_2$-specific GIF preparation indicated that the GIF bioactivity is associated with the peptide.

In order to characterize the peptide in the antigen-specific GIF preparations, the 231F1 cells were treated with anti-CD3, suspended in serum-free medium, and were cultured for 24 hr. in protein A-coated tissue culture dishes. Antigen-specific GIF binds to the monoclonal anti-TCRα chain, H28-710, coupled to Affigel (Iwata, et al., J. Immunol., 143:3917, 1989), therefore the culture supernatant was pre-absorbed with RGG-coupled Affigel and the flow through fraction was fractionated on H28-coupled Affigel. As expected, the majority (80–90%) of the GIF bioactivity in the culture supernatant bound to the immunosorbent, and was recovered by acid elution. No GIF bioactivity was detected in the acid eluate of RGG Affigel, which was employed for preabsorption. Analysis of the eluate fraction from H28-coupled Affigel by SDS-PAGE again demonstrated the 55 kDa peptide and 13 kDa peptide which bound anti-GIF (FIG. 1B; lane 1). Thus, the eluate fraction having the GIF titer of 1:80 was further fractionated on OVA-coupled Sepharose. Analysis of the fractions from the immunosorbent by SDS-PAGE and immunobloting indicated that the 55 kDa peptide as well as GIF bioactivity were recovered in the acid eluate but not detected in the flow through fraction. An important finding was that this 55 kDa peptide bound both anti-GIF and anti-TCRα chain in Western blottings (FIG. 1B, C).

As a control, similar experiments were carried out with culture supernatants of unstimulated 231F1 cells. Untreated 231F1 cells were suspended in serum-free media, and cultured in protein A-coated tissue culture flasks. The supernatant was pre-absorbed with RGG Affigel, and fractionated on H28-coupled Affigel. Bioactivity of the original culture supernatant of unstimulated cells was comparable to that of the culture supernatant of anti-CD3 simulated cells. However, the bioactivity was not detected in the acid eluate fraction of either the RGG Affigel or H28-710-Affigel. The latter fraction did not contain the 55 kDa peptide which bound H28-710 in a Western blot. Thus, the flow through fraction from the H28-710 Affigel was absorbed with anti-GIF Affigel and proteins retained in the column were recovered by acid elution. The eluate from anti-GIF-Affigel had GIF bioactivity and contained the 13 kDa peptide which bound anti-GIF in Western blot. As expected from previous observations (Jardieu, et al., supra), the GIF bioactivity in the culture supernatant of unstimulated 231F1 cells failed to bind to OVA-Sepharose, and the acid eluate fraction form OVA-Sepharose did not contain the 55 kDa peptide which bound anti-GIF in Western blot. The results indicated that the 55 kDa peptide is released from the 231F1 cells only when the cells were stimulated either with OVA-pulsed APC or by cross-linking of CD3 on the cell surface.

EXAMPLE 3

MOLECULAR CLONING OF TCRα CHAIN FROM Ts CELL

Figure 2B:
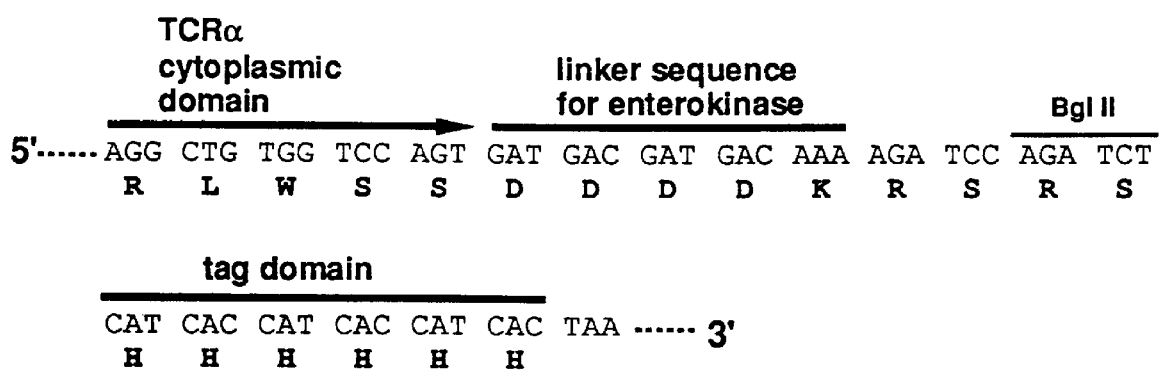
FIG. 2*a,* SEQ ID NOS. 1 and 2, and *b,* SEQ ID NOS. 3 and 4, show the nucleotide and deduced amino acid sequence of TCRα chain cDNA.
FIG. 2*c,* SEQ ID NOS. 5 and 6, shows the nucleotide and deduced amino acid sequence of murine GIF cDNA.
FIG. 2*d,* SEQ ID NOS. 7 and 8, shows the nucleotide and deduced amino acid sequence of human GIF cDNA.

The gene encoding TCRα chain from 231F1 cells was cloned by the method described by Inaba, et al. (Inaba, et al., supra). Double stranded cDNA were synthesized from mRNA of 231F1 cells and were circularized by litigation with T4 ligase. PCR was set up using an antisense oligonucleotide corresponding to the nucleotide 47–24 in Cα region gene and a sense oligonucleotide corresponding to the nucleotide 366–389 in the region (see Example 1). DNAs amplified in the PCR were subcloned and screened using Cα gene probe. Nucleotide sequence of the DNA insert in positive clones revealed the presence of a unique VαJα gene which is distinct from that derived from fusion partner BW5147. Among 5 DNA insert analyzed, 2 clones had the same sequence. The deduced amino acid sequence of the Vα region was identical to that of Vα11.3 (Jameson, et al., J. Immunol., 147:3185, 1991), except for 3 amino acids (FIG. 2). The Jα region in the VαJα gene from the 231F1 cells was unique but had 86% homology to Jα-3DT described by Kappler and Palomer (Yague, et al., Nucl. Acids Res., 16:11355, 1988). FIG. 2A shows the nucleotide sequence of fall length TCRα chain cDNA from 231F1 cells and deduced amino acid sequence. L,V,J,C indicate leader sequence, Vα, Jα, and Cα regions; FIG. 2B shows the nucleotide sequence of 3' end of Tag-TCRα cDNA.

To determine whether the unique TCRα chain in the 231F1 cell has complete Cα region, the Cα gene of the TCRα chain was cloned. Single stranded cDNAs were synthesized from 231F1 mRNA and PCR was set up using a primer specific for Vα11.3 (nucleotide 146–169 in FIG. 2) and oligo dT. The reaction mixture was diluted 100 fold, and the DNA fragments containing Cα gene were amplified by PCR using the nucleotide 213–234 in Vα11.3 and Cα3' end-specific primer. DNA fragments amplified by the second PCR were subdloned, and the nucleotide sequence of the insert was determined. The results indicated that 8 out of 9 clones obtained in the experiment have the complete nucleotide sequence of the Cα gene, and that the 231F1 cells have a unique TCRα chain whose complete sequence is shown in FIG. 2A.

Cloning of the full length TCRα-cDNA was completed by mixing equivalent amounts of the two cloned truncated fragments of TCRα cDNA corresponding to nucleotide 1-437 and 213-804 in PCR reaction buffer without primer. The full length cDNA thus obtained was amplified by PCR, and the cDNA inserted in pEFneo was transfected into the T cell line 175.2 which expresses TCRβ and the CD3, but lacks a functional TCRα gene (Glaichenhans, et al., supra). Stable transfectants were selected by Northern blotting of mRNA from each clone with Vα11.3 cDNA, and T cell clones expressing the highest amount of the α chain mRNA were established. A representative clone, E106, expressed TCRαβ and CD3 on the cell surface as determined by immunofluorescence, while the original 175.2 cell line cells could not be stained either by anti-CD3 or by anti-TCRβ chain. In order to confirm that the E106 cells synthesize TCRα chain, the stable transfectant was cultured in DMEM, and cell lysate from approximately $10^9$ cells was absorbed with H28-710-coupled to Affigel. Analysis of the acid eluate fraction from the immunosorbent by SDS-PAGE followed by immunoblotting with the mAb H28-710 revealed a 35 kDa peptide which bound the mAb.

Figure 3:
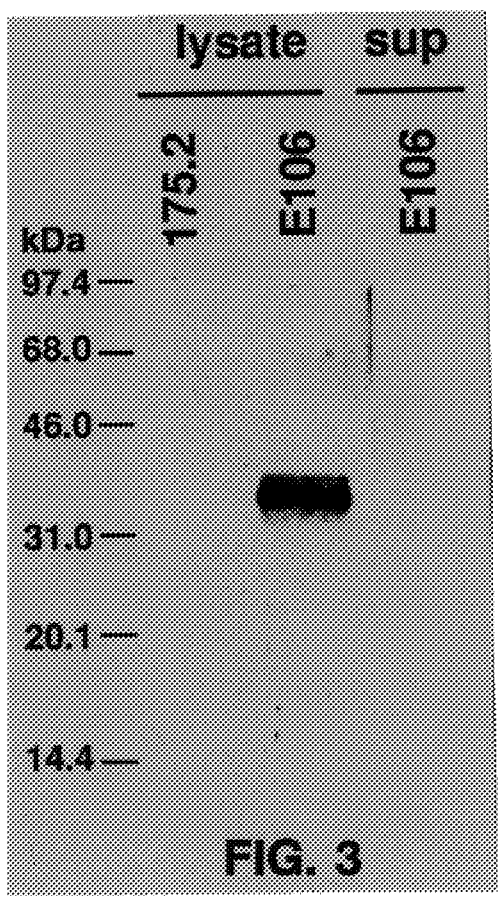
FIG. 3 shows an immunoblot analysis of TCRα chain from a stable TCRα chain cDNA transfectant.

As expected, the peptide was not detected when the cell lysate of the 175.2 clone was fractionated by the same procedures, and the acid eluate from the H28-710-Affigel was analyzed by immunoblotting. FIG. 3 shows an immunoblot analysis of TCRα chain from a stable transfectant E106. Cell lysate of E106 cells and untransfected 175.2 cell line cells were absorbed with H28-710-coupled Affigel, and proteins retained in the column were recovered by acid elution (lysate). E106 cells were stimulated with anti-CD3 and culture supernatant was fractionated on the same immunosorbent (sup). The eluate fractions were analyzed by immunoblotting with H28-710.

To test the possibility that E106 clone might release soluble TCRα chain or its derivative, the cells were stimulated with anti-CD3. The culture supernatant (300 ml) was concentrated, absorbed with RGG-coupled Affigel, and a flow-through fraction was fractionated on H28-710-coupled Affigel. Analysis of the acid eluate fraction by SDS-PAGE and immunoblotting failed to detect any peptide which bound the monoclonal anti-TCRα chain (FIG. 3). It appeared that the E106 cells failed to secrete TCRα chain or its derivative.

EXAMPLE 4

FORMATION OF A PRODUCT OF TCRα CHAIN GENE BY Ts CELLS

Since the Ts hybridoma, 231F1 forms antigen-specific GIF upon antigenic stimulation, and this factor binds to H-28-coupled Affigel, tests were performed to determine whether over-expression of TCRα chain in the Ts hybridoma might enhance the production of the antigen-specific factor. Thus, the TCRα chain cDNA was transfected into the Ts hybridoma to establish stable transfectants. The transfected cell clones were selected by Northern blot analysis of their mRNA using Vα11.3 cDNA fragment as a probe. Aliquots of a representative clone, 211α, which express the highest amount of Vα11.3$^+$ mRNA, were stimulated with anti-CD3 or cultured without stimulation. After a 24 hour culture in serum-free medium, culture supernatants were concentrated 20 fold, and analyzed by immunoblotting with the mAb H28-710.

Figures 4A, 4B:
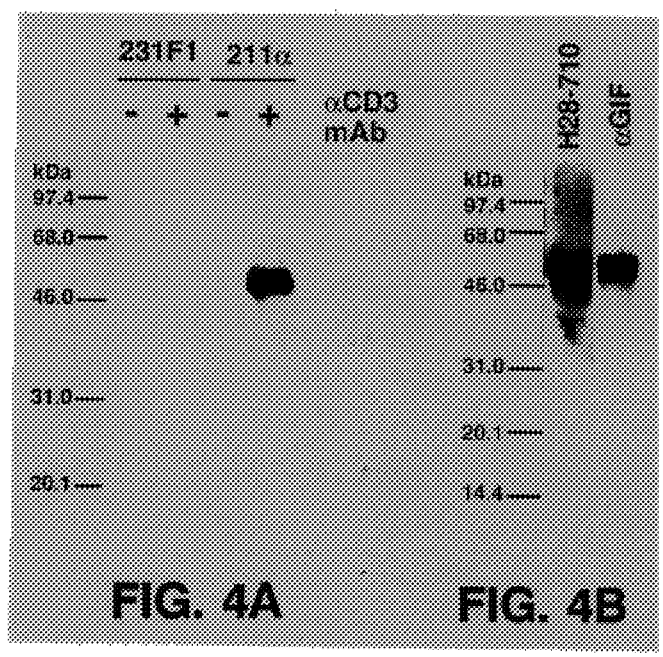
FIG. 4*a* and *b* show immunoblot analysis of culture supernatants from TCRα chain transfectants.

FIG. 4 shows the formation of a 55 kDa peptide by the stable transfectant of TCRα chain cDNA in 231F1 cells. FIG. 4A shows untransfected 231F1 cells and the stable transfectant 211α cells stimulated with anti-CD3. Culture supernatants of unstimulated (−) or anti-CD3-stimulated cells (+) were concentrated and analyzed by immunoblotting with H28-710. FIG. 4B shows culture supernatants of anti-CD3-stimulated 211α cells fractionated on H28-710 Affigel, and acid eluate fraction analyzed by immunoblotting with H28-710 or polyclonal anti-GIF.

As shown in FIG. 4A, culture supernatant of anti-CD3-stimulated 211α cells contained a 55 kDa peptide which bound the mAb H28, while the peptide was not detected in the culture supernatant of unstimulated cells. In order to confirm the specificity of immunoblotting, culture supernatant of anti-CD3-stimulated cells was absorbed with H28-710-coupled Affigel, and acid eluate fraction was analyzed by immunoblotting. As shown in FIG. 3B, the 55 kDa peptide was recovered in the acid eluate. As expected from previous observations with the culture supernatant of anti-CD3-stimulated 231F1 cells (FIG. 1), the 55 kDa peptide in the affinity-purified preparation bound not only H-28 but also anti-GIF, as determined by immunoblotting FIG. 4B. In agreement with this finding, the GIF bioactivity was detected in a 1:40 dilution of the acid eluate fraction, whereas the activity was not detectable in a 1:2 dilution of the flow through fraction from H-28 Affigel. Titration of GIF bioactivity in the original culture supernatant indicated that more than 50% of the activity in the culture supernatant was recovered in the acid eluate fraction from H-28 Affigel. Since the 55 kDa peptide is the only peptide having the GIF-determinant in the preparation (FIG. 4B), the GIF bioactivity appears to be associated with the peptide.

The stable transfectant of TCRα chain cDNA produced more 55 kDa peptide than the untransfected 231F1 cells. To confirm this observation, 231F1 cells were stimulated by anti-CD3 by the same procedures, and their culture supernatant was fractionated on the H28-710-Affigel. The majority of the GIF bioactivity in the original culture supernatant was recovered in the acid eluate fraction from the immunosorbent, and the fraction contained a 55 kDa peptide which bound both the mAb H28-710and anti-GIF in immunoblotting. Analysis of serial two fold dilutions of the affinity purified materials from the 211α cells and 231F1 cells by Western blot indicated that the 55 kDa peptide formed by the 211α cells was approximately 10 fold more than that produced by the same number of 231F1 cells. It was apparent that the transfection of TCRα chain cDNA markedly enhanced the formation of the peptide.

In order to confirm that the 55 kDa peptide is a product of the TCRα cDNA, a nucleotide sequence encoding a peptide of 6 histidine residues was attached at the 3' end of the TCRα chain cDNA (see FIG. 2B; nt sequence of 3' end of Tag-TCRα cDNA), and the TCRα-tag gene was transfected into the 231F1 cells. Aliquots of representative stable transfectants and untransfected 231F1 cells were stimulated with anti-CD3 or cultured without stimulation. A portion of concentrated culture supernatants were absorbed with Ni-NTA Agarose and proteins retained in the column were recovered by elution with 100 mM imidazole.

Figures 5A, 5B:
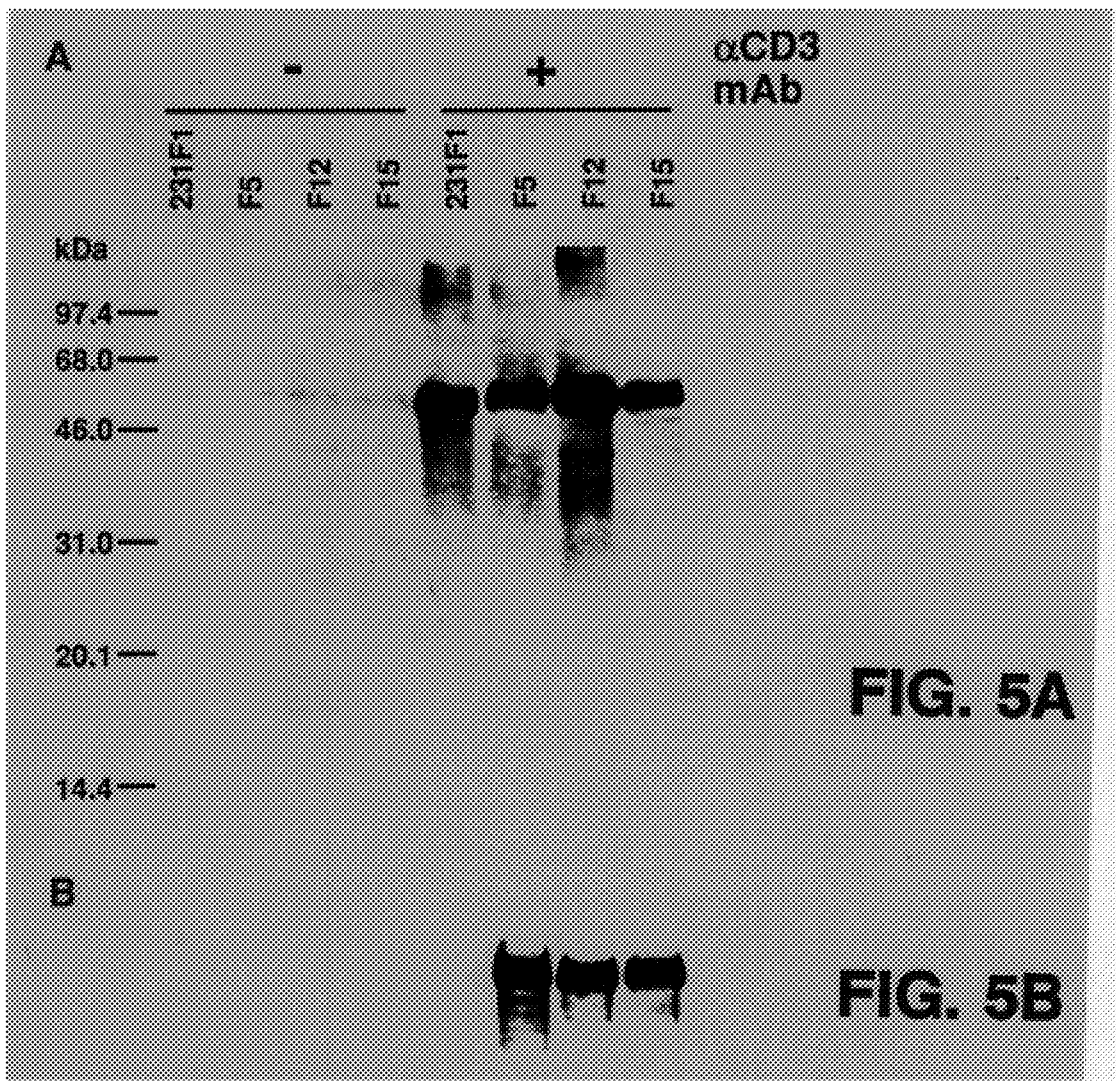
FIG. 5*a* and *b* show immunoblots of 55 kD antigen-specific GIF with His-tag from TCRα chain transfectants.

FIG. 5 shows the results of the formation of the 55 kDa peptide with His-tag by the stable transfectants of TCRα-tag gene in the 231F1 cells. As shown in FIG. 5A, aliquots of the stable transfectants, F5, F12 and F15, as well as untransfected 231F1 cells were cultured without stimulation (−) or after treatment with anti-CD3 mAb (+). Culture supernatants were concentrated, and analyzed by SDS-PAGE and immunoblotting with H28-710. Culture supernatants of anti-CD3 stimulated cell contained the 55 kDa peptide with TCRα-determinant. In FIG. 5B, His-containing peptide was affinity purified using Ni-NTA agarose, and the eluates were analyzed by immunoblotting with H28-710. The 55 kDa from the stable transfectants were affinity-purified, but the peptide from the 231F1 cells failed to bind to Ni-NTA agarose.

As shown in FIG. 5A, all of the culture supernatants of anti-CD3-stimulated cells contained a 55 kDa peptide which bound H28-710, whereas the peptide was not detected in the culture supernatants of unstimulated cells. The results also demonstrated that the 55 kDa peptide from the stable transfectants bound to Ni-NTA Agarose, but the same peptide from the 231F1 cells failed to do so (FIG. 5B).

In order to confirm that the 55 kDa peptide in the eluate of Ni-NTA Agarose is identical to that obtained from H-28 Affigel, a representative stable transfectant, F12, was stimulated with anti-CD3, and culture supernatants were fractionated either on Ni-NTA Agarose or on H28-710-coupled Affigel. Proteins retained in the absorbent were recovered by elution with imidazole or with glycine HCl buffer, pH 3.0 and analyzed by immunoblotting.

Figure 6:
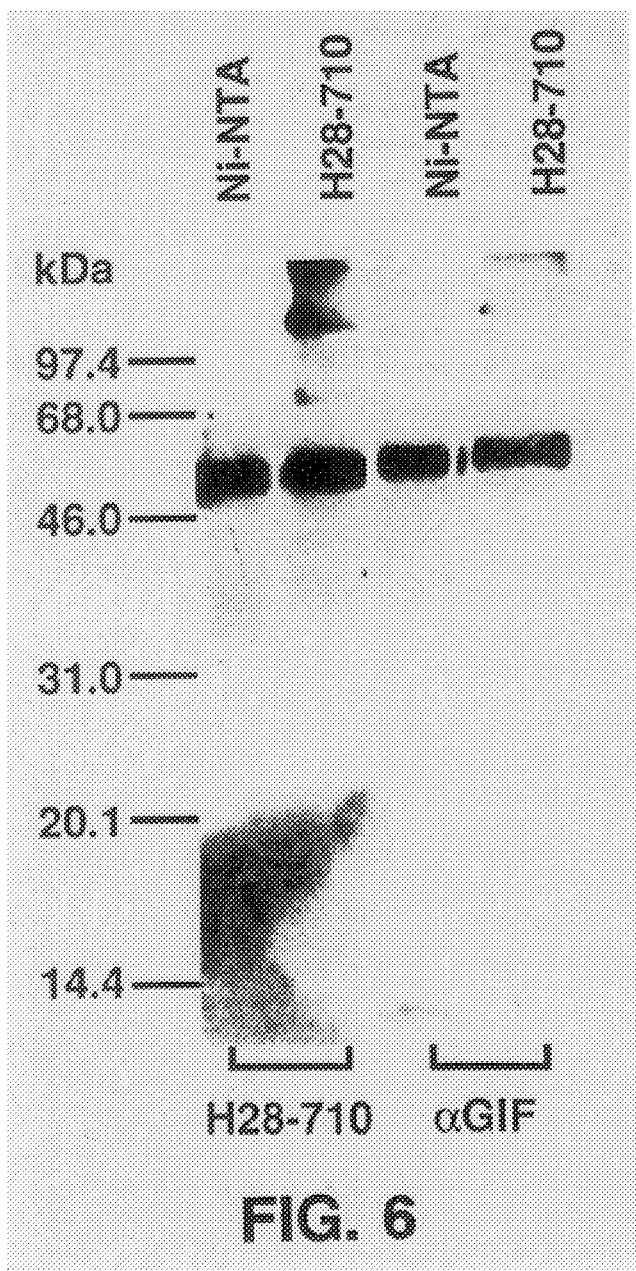
FIG. 6 shows an immunoblot of a TCRα-tag gene transfectant.

FIG. 6 shows that the stable transfectant of TCRα-tag gene in the 231F1 cells produce the 55 kDa peptide with His-tag. The F12 clone was stimulated by anti-CD3 and culture supernatant was fractionated in Ni-NTA agarose or H28-710Affigel. Eluates from the column were analyzed by immunoblotting with either monoclonal H28-710or polyclonal anti-GIF. The 55 kDa peptide having the Cα determinant and GIF determinant was detected in the eluate fraction from both Ni-NTA agarose and H28-710 Affigel.

As shown in FIG. 6, both preparations contained a 55 kDa peptide which bound H28-710 and polyclonal anti-GIF. As expected, the majority of GIF bioactivity in the culture supernatant bound to H-28 Affigel, and was recovered by acid elution. It was also found that the eluate fraction from Ni-NTA Agarose contained approximately ½ of GIF bioactivity present in the original culture supernatant. Although the remaining ½ of GIF bioactivity present in the original culture supernatant failed to be retained in Ni-NTA Agarose and was recovered in flow through fraction, the activity in the eluate fraction does not appear to be due to contamination because the column has been extensively washed with PBS containing 1 mM imidazoles prior to elution with 100 mM imidazole. Furthermore, GIF bioactivity in the culture supernatant of unstimulated F12 cells failed to be retained in Ni-NTA Agarose. The results collectively indicate that the 55 kDa peptide is a product of TCRα chain cDNA, and that the GIF bioactivity is associated with the peptide.

EXAMPLE 5

THE 55 kDa PEPTIDE IS A SUBUNIT OF ANTIGEN-SPECIFIC GIF

Experiments were carried out to determine whether the 55 kDa peptide actually represents antigen-specific GIF. The stable transfectant, 211α cells, were stimulated with anti-CD3, and culture supernatants were fractionated on a H28-710-coupled Affigel column. As expected, the 55 kDa peptide, possessing the TCRα determinant, bound to the immunosorbent and was recovered by elution at acid pH. The acid eluate was then fractionated on OVA-coupled Sepharose. Approximately ⅔ to ¾ of the GIF bioactivity in the eluate fraction from H-28 Affigel bound to OVA-Sepharose and was recovered by acid elution. Immunoblot analysis of both the acid eluate and flow through fractions from OVA-Sepharose showed that the 55 kDa peptide was detectable in the eluate fraction, however, the flow through fraction contained a substantially more 55 kDa peptide than the acid eluate fraction. The results indicate that the 55 kDa peptide is a subunit of antigen-specific GIF, but a fraction of the peptide released from the stable transfectant failed to bind to OVA-Sepharose.

Figure 7:
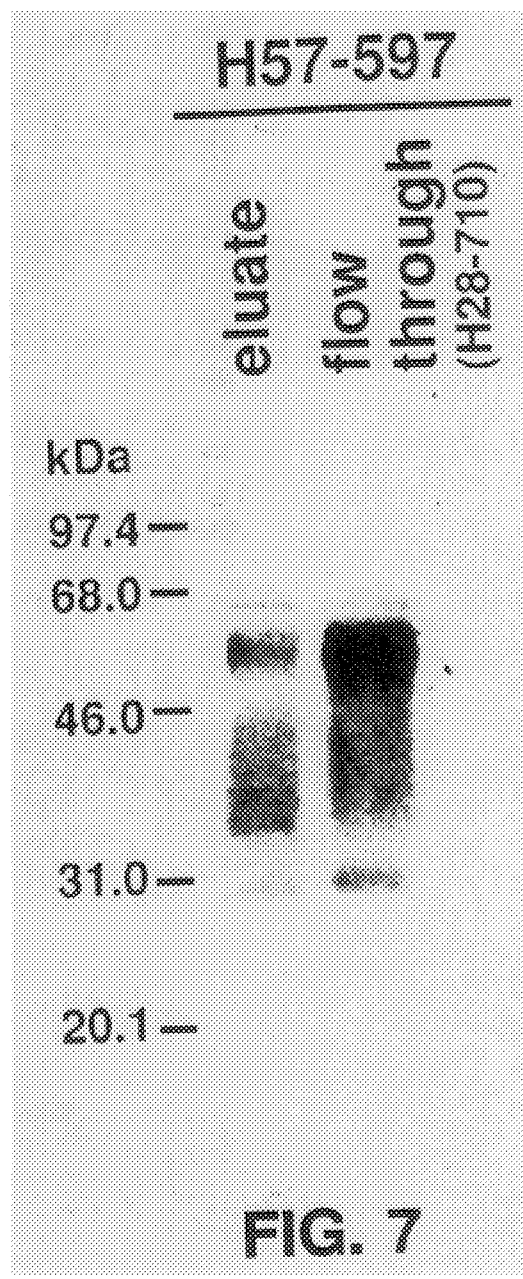
FIG. 7 shows an immunoblot analysis of 211α cells stimulated with anti-CD3. Lane 1 shows eluate fraction after anti-TCRβ and Lane 2 shows eluate from anti-TCRα.

Since previous studies indicated that the antigen-specific GIF from the 231F1 cells bound not only to anti-TCRα chain but also to mAb anti-TCRβ chain, i.e., H-57-597, coupled to Affigel (Iwata, et al., *J. Immunol.*, 143:3917, 1989), culture supernatants of anti-CD3-stimulated 211α cells were fractionated on a H57-597-coupled Affigel column. Proteins retained in the immunosorbent were recovered by acid elution. The flow-through fraction was absorbed with H28-710-Affi and proteins bound to the anti-TCRα immunosorbent were recovered. The eluate fractions from anti-TCRβ (lane 1) and anti-TCRα (lane 2) were analyzed by immunoblot with H28-710. As expected, the majority (70–80%) of the GIF bioactivity in the original culture supernatant was recovered in the acid eluate fraction from the H-57-597-column, and this fraction gave a 55 kDa band which bound the mAb H-28 in Western blot analysis (FIG. 7). However, the mAb H-57-597, failed to detect any peptide in the immunoblot analysis of the fraction. Thus, the flow through fraction from the H57-597-Affigel was absorbed with H28-Affigel, and proteins retained in the column were assessed for GIF bioactivity and immunoblotting. The results clearly showed that a substantial quantity of the H-28+, 55 kDa peptide failed to bind to H-57-597, but bound to H28-710-coupled Affigel. However, GIF bioactivity of the fraction was approximately by ¼ to ⅓ of that present in the eluate from H-57-597-Affigel. The results suggest that a minor fraction of the 55 kDa peptide is in complex with another peptide which reacts with H57-597, but a substantial fraction of the 55 kDa peptide secreted from the 211α cells is not associated with the peptide. While not wanting to be bound by a particular theory, one may speculate that association with the peptide, which bound to the anti-TCRβ antibody, is required for the binding of the 55 kDa GIF to antigen.

Although the invention has been described with reference to the presently preferred embodiment, it should be understood that various modifications can be made without departing from the spirit of the invention. Accordingly, the invention is limited only by the following claims.

We claim:

1. A method for the recombinant production of substantially pure biologically active antigen-specific glycosylation inhibiting factor (AgGIF) having a molecular weight of 55 kDa determined by reducing SDS-PAGE, said method comprising:
    a) culturing a host cell transfected with a polynucleotide sequence encoding a fusion polypeptide having a sequence with the formula: $R_1$–$R_2$, wherein $R_1$ is non-specific GIF and $R_2$ is a TCRα chain, under conditions which allow expression of the polynucleotide sequence; and
    b) isolating substantially pure AgGIF.

2. The method of claim 1, wherein $R_1$ is murine.

3. The method of claim 1, wherein $R_1$ is human.

4. The method of claim 1, wherein the host cell is a eukaryote.

5. The method of claim 4, wherein the host cell is a COS cell.

6. A method for the recombinant production of substantially pure biologically active antigen-specific glycosylation inhibiting factor (AgGIF) having a molecular weight of 55 kDa determined by reducing SDS-PAGE said method comprising:
    a) culturing a host cell transfected with a polynucleotide sequence encoding TCRα chain, under conditions which allow expression of the polynucleotide sequence, and wherein prior to transfection, the host cell expresses biologically active non-specific GIF; and
    b) isolating substantially pure AgGIF.

7. The method of claim 6, wherein the host cell is a Ts cell.

8. The method of claim 6, wherein the host cell is murine.

9. The method of claim 6, wherein the host cell is human.

10. The method of claim 6, further comprising TCRβ.

11. A method for the recombinant production of substantially pure biologically active antigen-specific glycosylation inhibiting factor (AgGIF) having a molecular weight of 55 kDa determined by reducing SDS-PAGE said method comprising:
    a) culturing a host cell co-transfected with a polynucleotide sequence encoding TCRα chain and a polynucleotide sequence encoding non-specific GIF fused to the 3' terminus of a polynucleotide sequence encoding at least a signal peptide for secretion, under conditions which allow expression of the polynucleotide sequences; and
    b) isolating substantially pure AgGIF.

12. The method of claim 11, wherein the polynucleotide sequence encoding non-specific GIF is fused to the 3' terminus of a polynucleotide sequence encoding an amino acid sequence comprising a signal peptide for secretion and a proteolytic cleavage site located downstream of the signal peptide.

13. The method of claim 12, wherein the amino acid sequence is an N-terminal proregion of human calcitonin precursor including the amino acid sequence Arg-X-Lys-Arg.

14. The method of claim 11, wherein the host cell is a mammalian cell.

15. The method of claim 11, wherein the host cell is a T cell.

16. The method of claim 1, wherein the culturing conditions include activating the host cell.

17. The method of claim 1, wherein the culturing conditions include causing translocation of the AgGIF through the endoplasmic reticulum.

18. The method of claim 6, wherein the culturing conditions include activating the host cell.

19. The method of claim 6, wherein the culturing conditions include causing translocation of the AgGIF through the endoplasmic reticulum.

20. The method as in claims 6 or 11, wherein conditions which allow expression of the polynucleotide sequence include stimulation with an antibody selected from the group consisting of anti-CD3 and anti-TCR to induce formation of AgGIF.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

-continued ( i ) SEQUENCE CHARACTERISTICS:
 ( A ) LENGTH: 804 base pairs
 ( B ) TYPE: nucleic acid
 ( C ) STRANDEDNESS: both
 ( D ) TOPOLOGY: both ( i i ) MOLECULE TYPE: cDNA ( x i ) SEQUENCE DESCRIPTION: SEQ ID NO:1:

| | | | | | |
|---|---|---|---|---|---|
| ATGCAGAGGA | ACCTGGGAGC | TGTGCTGGGG | ATTCTGTGGG | TGCAGATTTG | CTGGGTGAGC | 60 |
| GGAGATAAGG | TGAAGCAAAG | TCCCTCAGCG | CTGAGTCTCC | AAGAAGGAAC | CAATTCTGCT | 120 |
| CTGAGATGCA | ATTTTTCTAT | CGCCGCGACA | ACTGTGCAGT | GGTTCCTACA | GAATCCCAGG | 180 |
| GGCAGCCTCA | TGAATCTTTT | TTACCTGGTT | CCAGGAACAA | AGGAGAATGG | GAGGTTAAAG | 240 |
| TCAACATTCA | ATTCTAAGGA | GAGCTACAGC | ACCCTGCACA | TCAGGGATGC | CCAGCTGGAA | 300 |
| GACTCAGGCA | CTTACTTCTG | TGCTGCTGAG | GGGGGAGGCA | GCAATTACAA | ACTGACATTT | 360 |
| GGGAAAGGAA | CTCTCTTAAC | TGTGACTCCA | AACATCCAGA | ACCCAGAACC | TGCTGTGTAC | 420 |
| CAGTTAAAAG | ATCCTCGGTC | TCAGGACAGC | ACCCTCTGCC | TGTTCACCGA | CTTTGACTCC | 480 |
| CAAATCAATG | TGCCGAAAAC | CATGGAATCT | GGAACGTTCA | TCACTGACAA | AACTGTGCTG | 540 |
| GACATGAAAG | CTATGGATTC | CAAGAGCAAT | GGGGCCATTG | CCTGGAGCAA | CCAGACAAGC | 600 |
| TTCACCTGCC | AAGATATCTT | CAAAGAGACC | AACGCCACCT | ACCCCAGTTC | AGACGTTCCC | 660 |
| TGTGATGCCA | CGTTGACCGA | GAAAAGCTTT | GAAACAGATA | TGAACCTAAA | CTTTCAAAAC | 720 |
| CTGTCAGTTA | TGGGACTCCG | AATCCTCCTG | CTGAAAGTAG | CGGGATTTAA | CCTGCTCATG | 780 |
| ACGCTGAGGC | TGTGGTCCAG | TTGA | | | | 804 |

( 2 ) INFORMATION FOR SEQ ID NO:2:

( i ) SEQUENCE CHARACTERISTICS:
 ( A ) LENGTH: 267 amino acids
 ( B ) TYPE: amino acid
 ( D ) TOPOLOGY: linear ( i i ) MOLECULE TYPE: protein ( x i ) SEQUENCE DESCRIPTION: SEQ ID NO:2:

```
Met Gln Arg Asn Leu Gly Ala Val Leu Gly Ile Leu Trp Val Gln Ile
 1               5                  10                  15

Cys Trp Val Ser Gly Asp Lys Val Lys Gln Ser Pro Ser Ala Leu Ser
                20                  25                  30

Leu Gln Glu Gly Thr Asn Ser Ala Leu Arg Cys Asn Phe Ser Ile Ala
            35                  40                  45

Ala Thr Thr Val Gln Trp Phe Leu Gln Asn Pro Arg Gly Ser Leu Met
        50                  55                  60

Asn Leu Phe Tyr Leu Val Pro Gly Thr Lys Glu Asn Gly Arg Leu Lys
65                  70                  75                  80

Ser Thr Phe Asn Ser Lys Glu Ser Tyr Ser Thr Leu His Ile Arg Asp
                85                  90                  95

Ala Gln Leu Glu Asp Ser Gly Thr Tyr Phe Cys Ala Ala Glu Gly Gly
            100                 105                 110

Gly Ser Asn Tyr Lys Leu Thr Phe Gly Lys Gly Thr Leu Leu Thr Val
        115                 120                 125

Thr Pro Asn Ile Gln Asn Pro Glu Pro Ala Val Tyr Gln Leu Lys Asp
    130                 135                 140

Pro Arg Ser Gln Asp Ser Thr Leu Cys Leu Phe Thr Asp Phe Asp Ser
145                 150                 155                 160
```

| | | | | | | | | | | | | | | |
|---|---|---|---|---|---|---|---|---|---|---|---|---|---|---|
|Gln|Ile|Asn|Val|Pro<br>165|Lys|Thr|Met|Glu|Ser<br>170|Gly|Thr|Phe|Ile|Thr<br>175|Asp|
|Lys|Thr|Val|Leu<br>180|Asp|Met|Lys|Ala|Met<br>185|Asp|Ser|Lys|Ser|Asn<br>190|Gly|Ala|
|Ile|Ala|Trp<br>195|Ser|Asn|Gln|Thr|Ser<br>200|Phe|Thr|Cys|Gln|Asp<br>205|Ile|Phe|Lys|
|Glu|Thr<br>210|Asn|Ala|Thr|Tyr|Pro<br>215|Ser|Ser|Asp|Val|Pro<br>220|Cys|Asp|Ala|Thr|
|Leu<br>225|Thr|Glu|Lys|Ser|Phe<br>230|Glu|Thr|Asp|Met|Asn<br>235|Leu|Asn|Phe|Gln|Asn<br>240|
|Leu|Ser|Val|Met|Gly<br>245|Leu|Arg|Ile|Leu|Leu<br>250|Leu|Lys|Val|Ala|Gly<br>255|Phe|
|Asn|Leu|Leu|Met<br>260|Thr|Leu|Arg|Leu|Trp<br>265|Ser|Ser| | | | | |

(2) INFORMATION FOR SEQ ID NO:3:

(i) SEQUENCE CHARACTERISTICS:
        (A) LENGTH: 63 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:3:

```
AGGCTGTGGT  CCAGTGATGA  CGATGACAAA  AGATCCAGAT  CTCATCACCA  TCACCATCAC    60
TAA                                                                       63
```

(2) INFORMATION FOR SEQ ID NO:4:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:4:

| | | | | | | | | | | | | | | |
|---|---|---|---|---|---|---|---|---|---|---|---|---|---|---|
|Arg<br>1|Leu|Trp|Ser|Ser<br>5|Asp|Asp|Asp|Asp|Lys<br>10|Arg|Ser|Arg|Ser|His<br>15|His|
|His|His|His|His<br>20| | | | | | | | | | | | |

(2) INFORMATION FOR SEQ ID NO:5:

(i) SEQUENCE CHARACTERISTICS:
        (A) LENGTH: 635 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:5:

```
GGCACGACGT  CAGGTCCCTG  GCTTGGGTCA  CACCGCGCTT  TGTACCGTCC  TCCGGTCCAC    60
GCTCGCAGTC  TCTCCGCCAC  CATGCCTATG  TTCATCGTGA  ACACCAATGT  TCCCCGCGCC   120
TCCGTGCCAG  AGGGGTTTCT  GTCGGAGCTC  ACCCAGCAGC  TGGCGCAGGC  CACCGGCAAG   180
CCCGCACAGT  ACATCGCAGT  GCACGTGGTC  CCGGACCAGC  TCATGACTTT  TAGCGGCACG   240
AACGATCCCT  GCGCCCTCTG  CAGCCTGCAC  AGCATCGGCA  AGATCGGTGG  TGCCCAGAAC   300
CGCAACTACA  GTAAGCTGCT  GTGTGGCCTG  CTGTCCGATC  GCCTGCACAT  CAGCCCGGAC   360
```

```
CGGGTCTACA  TCAACTATTA  CGACATGAAC  GCTGCCAACG  TGGGCTGGAA  CGGTTCCACC    420

TTCGCTTGAG  TCCTGGCCCC  ACTTACCTGC  ACCGCTGTTC  TTTGAGCCTC  GCCTCTCCAC    480

GTAGTGTTCT  GTGTTTATCC  ACCGGTAGCG  ATGCCCACCT  TCCAGCCGGG  AGAAATAAAT    540

GGTTTATAAG  AGACCAAAAA  AAAAAAAAA   AAAAAAAAA   AAAAAAAAA   AAAAAAAAA     600

AAAAAAAAA   AAAAAAAAA   AAAAAAAAA   AAAAA                                 635
```

( 2 ) INFORMATION FOR SEQ ID NO:6:

( i ) SEQUENCE CHARACTERISTICS:
    ( A ) LENGTH: 115 amino acids
    ( B ) TYPE: amino acid
    ( D ) TOPOLOGY: linear ( i i ) MOLECULE TYPE: protein ( x i ) SEQUENCE DESCRIPTION: SEQ ID NO:6:

```
Met  Pro  Met  Phe  Ile  Val  Asn  Thr  Asn  Val  Pro  Arg  Ala  Ser  Val  Pro
 1              5                    10                            15

Glu  Gly  Phe  Leu  Ser  Glu  Leu  Thr  Gln  Gln  Leu  Ala  Gln  Ala  Thr  Gly
              20                        25                        30

Lys  Pro  Ala  Gln  Tyr  Ile  Ala  Val  His  Val  Val  Pro  Asp  Gln  Leu  Met
              35                        40                        45

Thr  Phe  Ser  Gly  Thr  Asn  Asp  Pro  Cys  Ala  Leu  Cys  Ser  Leu  His  Ser
         50                        55                        60

Ile  Gly  Lys  Ile  Gly  Gly  Ala  Gln  Asn  Arg  Asn  Tyr  Ser  Lys  Leu  Leu
 65                        70                        75                        80

Cys  Gly  Leu  Leu  Ser  Asp  Arg  Leu  His  Ile  Ser  Pro  Asp  Arg  Val  Tyr
                   85                        90                        95

Ile  Asn  Tyr  Tyr  Asp  Met  Asn  Ala  Ala  Asn  Val  Gly  Trp  Asn  Gly  Ser
                  100                       105                      110

Thr  Phe  Ala
         115
```

( 2 ) INFORMATION FOR SEQ ID NO:7:

( i ) SEQUENCE CHARACTERISTICS:
    ( A ) LENGTH: 557 base pairs
    ( B ) TYPE: nucleic acid
    ( C ) STRANDEDNESS: both
    ( D ) TOPOLOGY: both ( i i ) MOLECULE TYPE: cDNA ( x i ) SEQUENCE DESCRIPTION: SEQ ID NO:7:

```
CAGGCACGTA  GCTCAGCGGC  GGCGCGGCGC  GTGCGTCTGT  GCCTCTGCGC  GGGTCTCCTG     60

GTCCTTCTGC  CATCATGCCG  ATGTTCATCG  TAAACACCAA  CGTGCCCCGC  GCCTCCGTGC    120

CGGACGGGTT  CCTCTCCGAG  CTCACCCAGC  AGCTGGCGCA  GGCCACCGGC  AAGCCCCCC     180

AGTACATCGC  GGTGCACGTG  GTCCCGGACC  AGGTCATGGC  CTTCGGCGGC  TCCAGCGAGC    240

CGTGCGCGCT  CTGCAGCCTG  CACAGCATCG  GCAAGATCGG  CGGCGCGCAG  AACCGCTCCT    300

ACAGCAAGCT  GCTGTGCGGC  CTGCTGGCCG  AGCGCCTGCG  CATCAGCCCG  GACAGGGTCT    360

ACATCAACTA  TTACGACATG  AACGCGGCCA  ATGTGGGCTG  GAACAACTCC  ACCTTCGCCT    420

AAGAGCCGCA  GGGACCCACG  CTGTCTGCGC  TGGCTCCACC  CGGGAACCCG  CCGCACGCTG    480

TGTTCTAGGC  CCGCCCACCC  CAACCTTCTG  GTGGGGAGAA  ATAAACGGTT  TAGAGACTAA    540

AAAAAAAAAA  AAAAAA                                                        557
```

( 2 ) INFORMATION FOR SEQ ID NO:8:

( i ) SEQUENCE CHARACTERISTICS:
        ( A ) LENGTH: 115 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Pro Met Phe Ile Val Asn Thr Asn Val Pro Arg Ala Ser Val Pro
 1           5                      10                  15
Asp Gly Phe Leu Ser Glu Leu Thr Gln Gln Leu Ala Gln Ala Thr Gly
            20                  25                  30
Lys Pro Pro Gln Tyr Ile Ala Val His Val Val Pro Asp Gln Val Met
        35                  40                  45
Ala Phe Gly Gly Ser Ser Glu Pro Cys Ala Leu Cys Ser Leu His Ser
    50                      55                  60
Ile Gly Lys Ile Gly Gly Ala Gln Asn Arg Ser Tyr Ser Lys Leu Leu
65                      70                  75                  80
Cys Gly Leu Leu Ala Glu Arg Leu Arg Ile Ser Pro Asp Arg Val Tyr
                85                      90                  95
Ile Asn Tyr Tyr Asp Met Asn Ala Ala Asn Val Gly Trp Asn Asn Ser
            100                 105                 110
Thr Phe Ala
        115
```